(12) United States Patent
Graetz et al.

(10) Patent No.: US 7,326,355 B2
(45) Date of Patent: Feb. 5, 2008

(54) MOBILE FILTRATION FACILITY AND METHODS OF USE

(75) Inventors: Gary Graetz, Smithfield, UT (US); Tracy Zilles, River Heights, UT (US)

(73) Assignee: Hyclone Laboratories, Inc., Logan, UT (US)

( * ) Notice: Subject to any disclaimer, the term of this patent is extended or adjusted under 35 U.S.C. 154(b) by 485 days.

(21) Appl. No.: 10/929,275

(22) Filed: Aug. 30, 2004

(65) Prior Publication Data

US 2005/0218075 A1    Oct. 6, 2005

Related U.S. Application Data

(60) Provisional application No. 60/558,196, filed on Mar. 31, 2004.

(51) Int. Cl.
*B01D 61/00* (2006.01)
*E04H 1/00* (2006.01)
*B65B 3/04* (2006.01)

(52) U.S. Cl. .................. 210/806; 52/79.1; 52/79.7; 52/143; 210/650; 210/651; 210/767; 422/44; 422/99; 422/187; 435/2; 141/10; 141/18; 141/67

(58) Field of Classification Search ................ 210/252, 210/257.1, 258, 259, 260, 483, 488, 490, 210/650, 651, 767, 805, 806; 604/4.01, 6.09, 604/28, 65; 422/44; 435/2
See application file for complete search history.

(56) References Cited

U.S. PATENT DOCUMENTS

| | | | |
|---|---|---|---|
| 3,939,623 A | * | 2/1976 | Shine et al. ................ 53/440 |
| 3,986,506 A | * | 10/1976 | Garber et al. ............... 604/406 |
| 4,095,658 A | * | 6/1978 | Kendall et al. ............. 177/118 |
| 4,754,786 A | | 7/1988 | Roberts |
| 5,033,649 A | | 7/1991 | Copeland et al. |
| 5,195,922 A | | 3/1993 | Genco |
| 5,350,080 A | | 9/1994 | Brown et al. |
| 5,362,642 A | | 11/1994 | Kern |
| 5,431,599 A | | 7/1995 | Genco |

(Continued)

FOREIGN PATENT DOCUMENTS

EP    0 267 560 A1    5/1988

OTHER PUBLICATIONS

*The Flexel 3-D System*, Stedim, Inc., 1998.

(Continued)

*Primary Examiner*—John Kim
(74) *Attorney, Agent, or Firm*—Workman Nydegger

(57) ABSTRACT

A mobile first housing bounds a substantially sterile clean room, a filtration room, and at least one change room communicating between clean room. A fluid filtration system is disposed within the first housing, the filtration system includes a first support container in which a disposable fill bag is disposed. A disposable fluid line extends between the fill bag and the at least one filter. A support bin is also disposed within the first housing. A disposable pooling bag is disposed within the support bin, the pooling bag being in fluid communication with the at least one filter. A disposable fill line has a first end in fluid communication with the pooling bag and an opposing second end disposed within the clean room.

14 Claims, 17 Drawing Sheets

U.S. PATENT DOCUMENTS

| | | | |
|---|---|---|---|
| 5,584,327 | A | 12/1996 | Thomas et al. |
| 5,656,491 | A | 8/1997 | Cassani et al. |
| 5,941,867 | A | 8/1999 | Kao |
| 6,071,005 | A | 6/2000 | Ekambaram et al. |
| 6,083,587 | A | 7/2000 | Smith et al. |
| 6,086,574 | A | 7/2000 | Carroll et al. |
| 6,168,718 | B1 * | 1/2001 | Sutter et al. ............... 210/651 |
| 6,186,932 | B1 | 2/2001 | Vallot |
| 6,302,299 | B1 | 10/2001 | Baker et al. |
| 6,450,215 | B1 | 9/2002 | Willemstyn |
| 6,494,613 | B2 | 12/2002 | Terentiev |
| 6,670,171 | B2 | 12/2003 | Carll |
| 6,695,803 | B1 * | 2/2004 | Robinson et al. .......... 604/4.01 |
| 6,709,862 | B2 | 3/2004 | Curtis |
| 6,808,638 | B1 * | 10/2004 | Purdum ..................... 210/748 |
| 6,994,790 | B2 * | 2/2006 | Corbin et al. ............... 210/639 |
| 7,153,021 | B2 * | 12/2006 | Goodwin et al. ........... 366/273 |
| 2002/0131654 | A1 | 9/2002 | Smith et al. |
| 2003/0077466 | A1 | 4/2003 | Smith et al. |
| 2003/0144646 | A1 | 7/2003 | Se et al. |
| 2004/0027912 | A1 | 2/2004 | Bibbo et al. |
| 2004/0062140 | A1 | 4/2004 | Cadogan et al. |
| 2004/0159616 | A1 | 8/2004 | Cohee et al. |
| 2004/0190372 | A1 | 9/2004 | Goodwin et al. |
| 2004/0261889 | A1 | 12/2004 | Elgan et al. |

OTHER PUBLICATIONS

C. R. Valeri et al., *Evaluation of the Sterimatics ST-30 System for Preparing Sterile, Pyrogen Free Water; Lactated Ringer's Resuscitative Fluid; Intravenous Sodium Chloride Solution; and Sodium Chloride-Glucose-Phosphate Solution Used in the Deglycerolization of Human Red Cells Frozen with 40% W.V. Glycerol* (Feb. 1984-Sep 1985), Office of Naval Research Contract N000014-79-C-0168, Technical Report 86-01, Mar. 10, 1986.

* cited by examiner

MOBILE FILTRATION FACILITY AND METHODS OF USE

CROSS-REFERENCE TO RELATED APPLICATIONS

This application claims priority to U.S. Provisional Application Ser. No. 60/558,196, filed Mar. 31, 2004, which is incorporated herein by specific reference.

BACKGROUND OF THE INVENTION

1. The Field of the Invention

The present invention relates to mobile filtration facilities used in filtering liquids derived from mammalian blood and other fluids.

2. The Relevant Technology

Mammalian blood serum, such as fetal bovine serum, calf serum, and the blood serum of other mammals, is broadly used in the growth and development of cell cultures. Although serum can be derived from the blood of all animals, it has been found that serum derived from a fetus or new born has enhanced properties for cell growth. In part, this is because such serums are high in growth factors and hormones which enhance cell growth.

Most mammalian blood serum is obtained at established slaughterhouses. For example, fetal bovine serum is typically obtained from fetuses that are removed from cattle that are slaughtered for beef. The fetuses are taken to an area of the slaughterhouse where the blood is harvested from the fetuses. The blood is then processed so as to remove the serum component. The raw unfiltered serum is then placed in bottles and quickly frozen.

Because there are relatively few fetuses and such fetuses have a rather small amount of blood, fetal bovine serum is a precious and expensive commodity. Prior to use of the serum, the serum must be filtered under highly stringent conditions that require the use of a sterile clean room. Furthermore, most filtering processes pass the serum through different stainless steel tanks and fixed lines that must be repeatedly cleaned and certified between batches. This cleaning requires the use and disposal of hazardous cleaning chemicals. Although a clean room and the required filtering equipment can be erected at each slaughterhouse, this is generally not cost efficient. That is, because there is such a small volume of fetal bovine serum harvested at a given slaughterhouse, it is difficult for a single slaughterhouse to recoup the expense of building, operating, manning, and maintaining a sterile clean room and the filtration equipment.

As a result, the traditional approach to filtering serum is to ship the serum to an established filtration facility. The problem with this approach, however, is that slaughterhouses are widely spaced apart throughout the world and there are relatively few filtration facilities. Because serum must remain frozen, the serum becomes relatively expensive to ship over long distances to the established filtration facilities. Furthermore, because of various blood diseases, some countries will not allow blood products to be transported into their country for filtering and/or sale.

In addition, it is often critically important to the purchasers of filtered serum that they can establish and certify where a particular serum was derived and filtered. Acquiring a serum in one country, filtering the serum in a second country, and then attempting to sell the serum in a third country is largely prohibitive. Such movement between countries makes it difficult to obtain required import licenses and to provide sufficient assurance to the end purchasers as to the origin and history of the serum.

Similar types of problems are also encountered in filtering blood components which are used in clinical chemistry controls. For example, human donated blood that has expired is typically processed to extract the serum, plasma, and fractions thereof which can subsequently be used in clinical chemistry controls. Again, prior to use such blood components must be filtered under highly stringent conditions that require the use of a sterile clean room and a filtration system. The expired blood is often found at blood banks and other storage facilities located at sporadic locations throughout the world. As with fetal bovine serum, filtering the blood components is cost prohibitive to the storage facilities. The blood and/or bloods products are thus typically shipped to filtration facilities. Again, however, the shipping of blood products requires refrigerated shipping which adds significant cost to the final blood products. Furthermore, attempts to transport blood products between different countries can be problematic.

Accordingly, what is needed are methods and systems that can be used to efficiently filter and/or sterilize blood products and other types of liquids that are produced and/or collected at different facilities around the world.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to mobile filtration facilities and methods of use. In one embodiment the mobile filtration facilities can be used in the filtration and/or sterilization of mammalian blood components such as serum, plasma, and fractions thereof. Such blood components can be derived from human and non-human mammals. For example, as used in the specification and appended claims, the term "mammalian blood serum" is broadly intended to include fetal bovine serum, calf serum, and the blood serum of other mammals such as horses, pigs, sheep, and the like. Mammalian blood serum can also comprise serum derived from donated human blood. In alternative embodiments, the mobile filtration facilities can be used in the filtration and/or sterilization of media, buffers, and regents used in the growth of cell cultures and in still other liquids which require filtration and/or sterilization.

Figure 1:
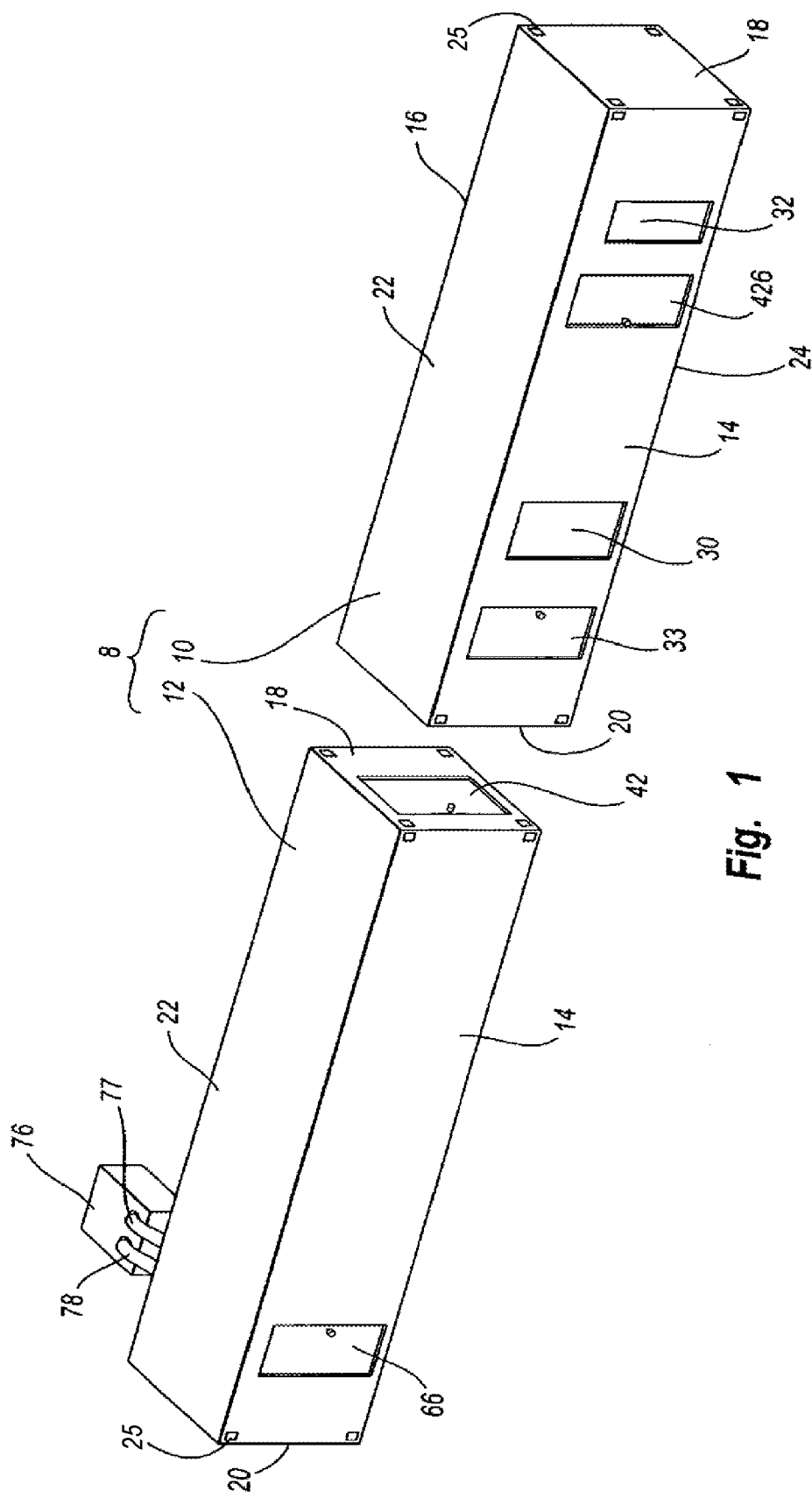
FIG. 1 is a perspective view of a filtration facility including a first housing and a second housing.

Depicted in FIG. 1 is one embodiment of an inventive mobile filtration facility 8 incorporating features of the present invention. Filtration facility 8 comprises a mobile first housing 10 and a mobile second housing 12. Each housing 10 and 12 has a substantially parallelepiped configuration that includes a front wall 14 and an opposing back wall 16 that each extend between a first end wall 18 and an opposing second end wall 20. Each housing 10 and 12 also includes a flat roof 22 and a floor 24. Hooking ports 25 are formed on each corner of each housing 10 and 12 to facilitate attachment to housings 10 and 12 for lifting.

In one embodiment, each of first housing 10 and second housing 12 comprises a standard metal shipping container having standard dimensions. For example, containers intended for intercontinental use typically have external standard dimensions of length 20 feet (6.10 m), 30 feet (9.14 m), or 40 feet (12.20 m); width of 8 feet (2.44 m); and height of 8.5 feet (2.59 m) or 9.5 feet (2.90 m). These dimensions are only approximations and can vary within a few inches. For example, the 30 feet containers are typically closer to 29.9375 feet (9.125 m) in length. Other standard and non-standard dimensions can also be used. In the illustrated example of the present invention, each of first housing 10 and second housing 12 has a length of 40 feet (12.20 m), a width of 8 feet (2.44 m), and height between 8.5 feet (2.59 m) to 9.5 feet (2.90 m) each within a tolerance of a few inches, such as within six inches (0.15 m).

By forming the filtration facility 8 out of standard shipping containers, housings 10 and 12 can be stacked, if desired, and easily transported by rail, ship, truck or the like using conventional techniques. In an alternative embodiment, housings 10 and 12 can be custom designed having other dimensions. In such other embodiments, roof 22 can be pitched.

Figure 2:
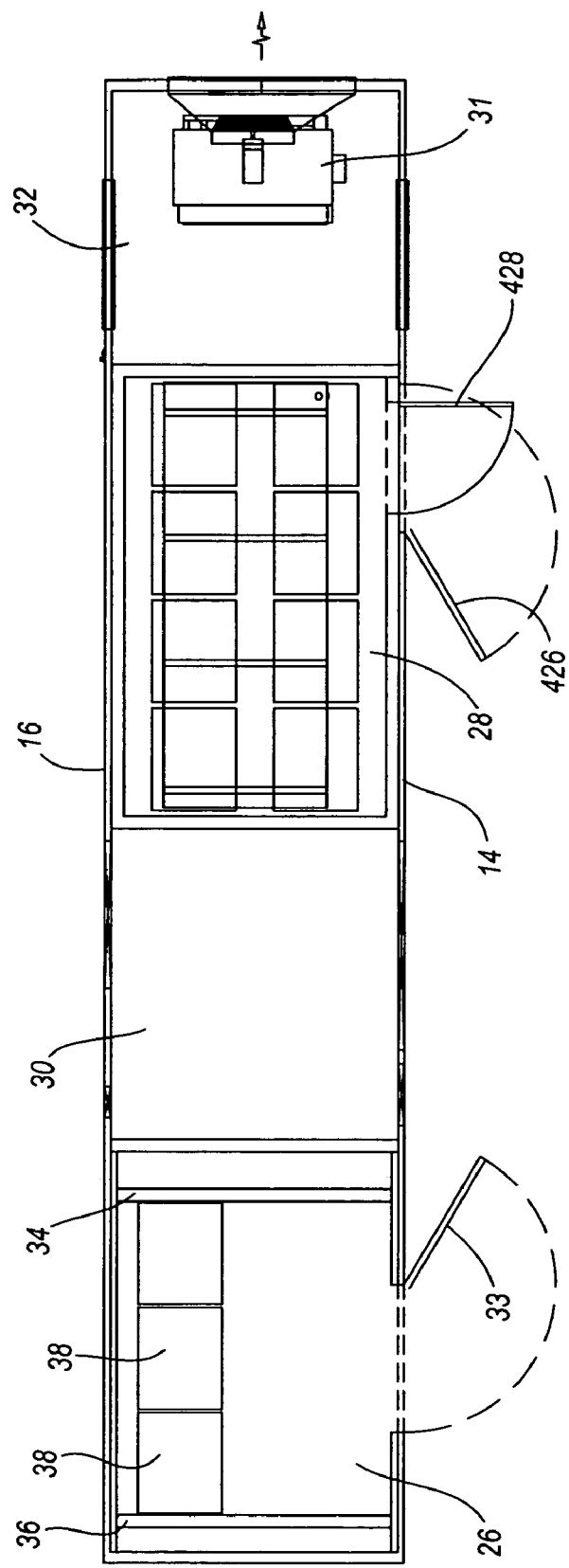
FIG. 2 is a top cross sectional plan view of the first housing shown in FIG. 1.

As depicted in FIGS. 1 and 2, first housing 10 comprises a thaw room 26 and a quick freezer room 28. A storage room 30 houses the heating and ventilation equipment that regulates the air flow and temperature within thaw room 26 while a storage room 32 houses the compressor and other equipment 31 needed to control the temperature within freezer room 28.

Thaw room 26 is accessed through a door 33 and is partially bounded by a first wall 34 and an opposing second wall 36. First wall 34 is substantially covered with inlet vents from floor to ceiling while second wall 36 is substantially covered with return vents from floor to ceiling. Heated air is uniformly blown through all of the inlet vents on first wall 34 and simultaneously drawn out through all of the return vents on second wall 36. As a result, an airflow, which is substantially uniform from floor 24 to roof 22, continually passes across thaw room 26 from first wall 34 to second wall 36.

For purposes of illustration, the inventive filtration facility 8 will be discussed below in terms of filtering fetal bovine serum. It is emphasized that in alternative embodiments filtration facility 8 can be used in filtering other blood components, other types of serum, media, reagent, buffers, and other types of fluids.

Fetal bovine serum is initially harvested at a facility such as a slaughterhouse. The fetal bovine blood is collected and then processed to extract the serum. Specifically, the collected blood is clotted and then passed through a centrifuge so as to remove the clotted portion. The remaining clear fluid portion of the blood is the raw or unfiltered serum. The unfiltered serum is placed in plastic bottles and then stored within a freezer at a storage site so as to remain frozen. The storage site is typically located at or close to the harvesting facility. In one embodiment the plastic bottles hold a volume of 2 liters. Other sized bottles can also be used. When a sufficient quantity of the unfiltered serum has been collected and frozen, the inventive filtration facility 8 is transported to the storage site. Housings 10 and 12 are positioned within a warehouse or other temporary shelter and connected to a source of water and electrical power. In alternative embodiments housings 10 and 12 can be insulated and otherwise designed for operating in an exposed environment.

To initiate processing, a first batch of frozen serum is placed within thaw room 26. Although filtration facility 8 can operate in a continuous flow manner, the serum is typically processed on a batch basis so that an entire batch can be certified as having common defined properties. For example, as will be discussed below in greater detail, once a batch of serum is filtered, the filtered serum is bottled and marked with a specific lot number. End purchasers and users will understand that all filtered serum having a common lot number has substantially identical properties. As such, use of serum from different bottles having the same lot number should produce substantially the same results. The batch size can be any desired volume such as 50 liters, 500 liters, 1,000 liters, 2,000 liters or the like. It is noted that the initial batch of unfiltered serum can comprise bottles of unfiltered serum derived under different conditions, i.e., different processing facilities and or different herds of animals.

In the present example, the batch size is 1,000 liters. As such, five hundred of the 2 liter bottles containing the frozen unfiltered serum are placed on wire shelves of transportable carts 38. Carts 38 are wheeled into thaw room 26 so as to substantially fill thaw room 26 from floor to ceiling. Each 2 liter bottle is spaced apart on cart 38 so that air can freely flow around all side of each bottle. Sizing carts 38 so that the bottles uniformly extend between the floor and ceiling of thaw room 26 forces the air to flow between the bottles as opposed to simply flowing over top of or below the carts and bottles. The air blowing into thaw room 26 is set at approximately 32° C. so that the frozen unfiltered serum gradually thaws in approximately 10 hours. Other temperatures and thaw rates can also be used.

Figure 3:
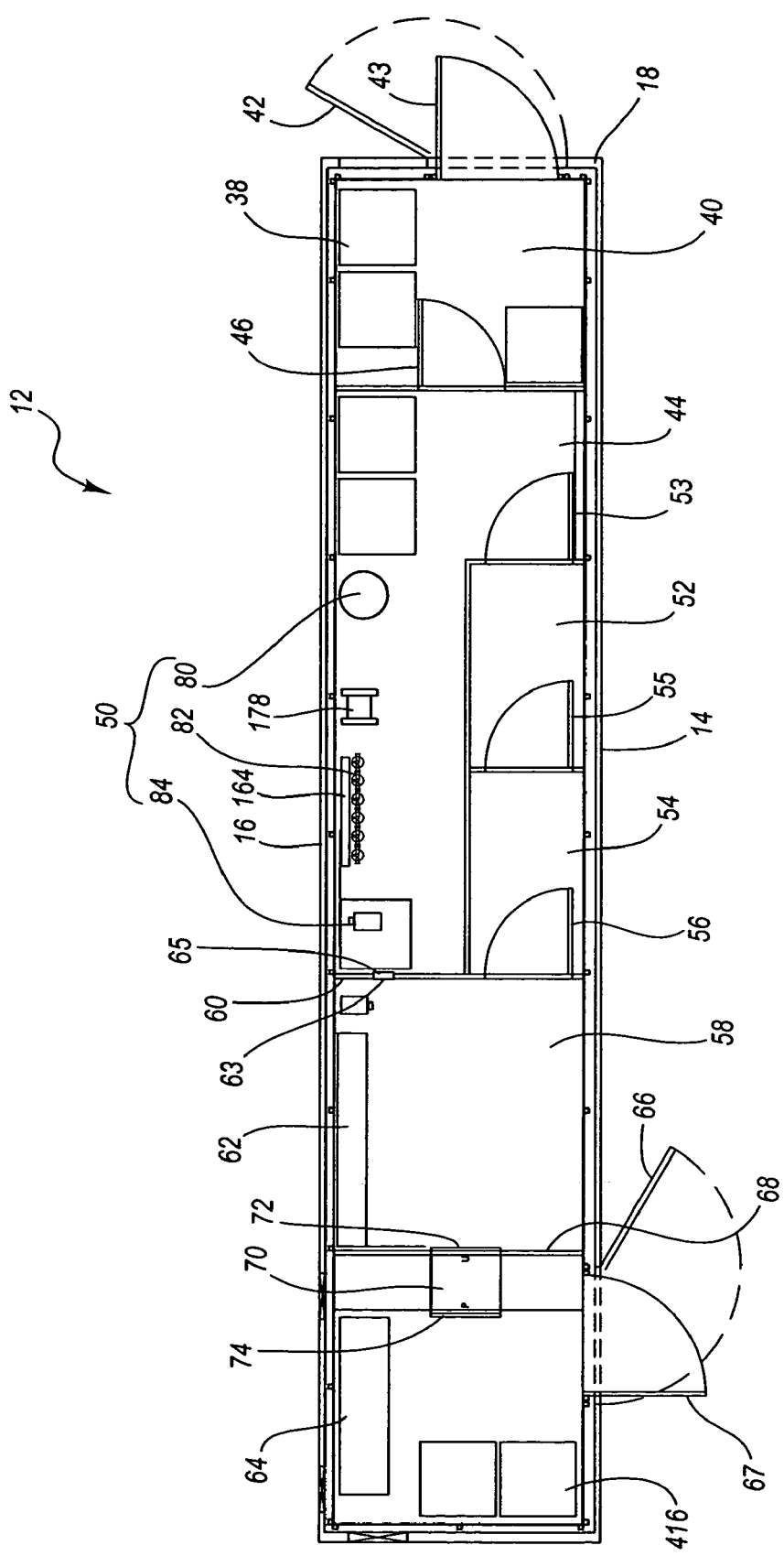
FIG. 3 is a top cross sectional plan view of the second housing shown in FIG. 1.

Once the unfiltered serum is thawed, select carts 38 containing the thawed unfiltered serum are wheeled from thaw room 26 to a staging room 40 of second housing 12. As depicted in FIG. 3, second housing 12 comprises staging room 40 which is accessed through a first door 42 and a second door 43 each on first end wall 18. First door 42 is made of a heavy gauge metal that provides protection for second door 43 during shipping and transport. In alternative embodiments, first door 42 can be eliminated. Staging room 40 communicates with a non-sterile filtration room 44 through a door 46. As will be discussed below in greater detail, substantially disposed within filtration room 44 is a filtration system 50.

Staging room 40 and filtration room 44 combine to form a filtration area. Accessible from filtration room 44 through a door 53 is a first change room 52. First change room 52 accesses a second change room 54 through a door 55. From second change room 54, a clean room 58 is accessed through a door 56. Disposed within clean room 58 is a laminar hood 62. In one embodiment, laminar hood 62 comprises a Federal Standard Class 100 (ISO Class 5) laminar air flow hood. In alternative embodiments, depending largely upon the type of material being filtered, laminar hood 62 can have a more stringent or less stringent classification. A wall 60 is formed between clean room 58 and filtration room 44. As discussed below in greater detail, a pass-through opening 63 is formed on wall 60. A window 65 is slidable mounted within pass-though opening 63 so as to selectively open and close pass-through opening 63.

Second housing 12 also comprises a packing room 64 which is accessed through an exterior first door 66 and a second door 67 on front wall 14. Again, first door 66 provides protection for second door 67 and can be eliminated. A partition wall 68 separates clean room 58 from packing room 64. A small pass-through portal 70 extends through partition wall 68 so as to allow bottles of filtered serum to be passed between clean room 58 and packing room 64. Mounted on opposing ends of pass-through portal 70 is a first sliding door 72 and a second sliding door 74.

In one embodiment each of the rooms of second housing 12 are designed with conventional clean room standards. For example, all of the wall are formed from steel panels having powdered coated paint. The joints of intersecting panels are sealed by caulking. All doors are also steel panel doors. The window and door frames are also designed to be flush with the walls so as to minimize any ledges. In alternative embodiments the walls and doors can be made from other materials or have different configurations.

As depicted in FIG. 1, a modular air filtration system 76 is positioned outside of second housing 12 after housing 12 is positioned for operation. An air inlet duct 77 and an air outlet duct 78 are positioned so as to extend between air filtration system 76 and housing 12. Specifically, ducts 77 and 78 couple with duct work formed in roof 22 of second housing 12 such that air filtration system 76 filters the air within clean room 58 and change rooms 52 and 54. Air filtration system 76 can also be used to filter the air within the other rooms of second housing 12 such as filtration room 44. To further facilitate air filtration, in one embodiment 99.995% HEPA filters are located at each air inlet vent for each room of second housing 12. The HEPA filters can be limited to just clean room 58 and/or can have a lower particle removal percentage for other applications.

It is noted that second housing 12 is configured so that air filtration system 76 creates a positive air pressure within clean room 58 relative to all other adjacent rooms. In one embodiment this is accomplished by restricting the air return vents of clean room 58 relative to the air inlet vents thereof so as to produce a positive air pressure within clean room 58. As a result, any leaks between the rooms results in air flowing from clean room 58 to the adjacent room, thereby preventing contaminated air from entering clean room 58. For examples, doors 72 and 74 on opposing ends of pass-through portal 70, FIG. 3, are designed to be loose fitting so that filtered air within clean room 58 is continually flowing from clean room 58, through pass-through portal 70, and into packing room 64. Likewise, air flows from clean room 58 through any leaks in pass-though opening 63 into filtration room 44.

In one embodiment, housing 12 with the rooms thereof and air filtration system 76 are designed so that clean room 58 meets Federal Standard Class 1000 (ISO Class 6) requirements. In other embodiments, depending on what is being filtered, clean room 58 can be designed to meet more stringent, i.e., ISO Class 5, or less stringent Class requirements. Depending on the desired Class for clean room 58, it is appreciated that one of change rooms 52 or 54 could be eliminated. Furthermore, it is noted that the various rooms can be moved around. For example, first change room 52 can be designed to be directly accessed from staging room 40, from packing room 64, or from the exterior. In the depicted design, an operator enters through staging room 40 and then subsequently passes through filtration room 44, first change room 52, second change room 54, and then into clean room 58. Each room is entered by a door and each room is designed to be increasingly clean.

Figure 4:
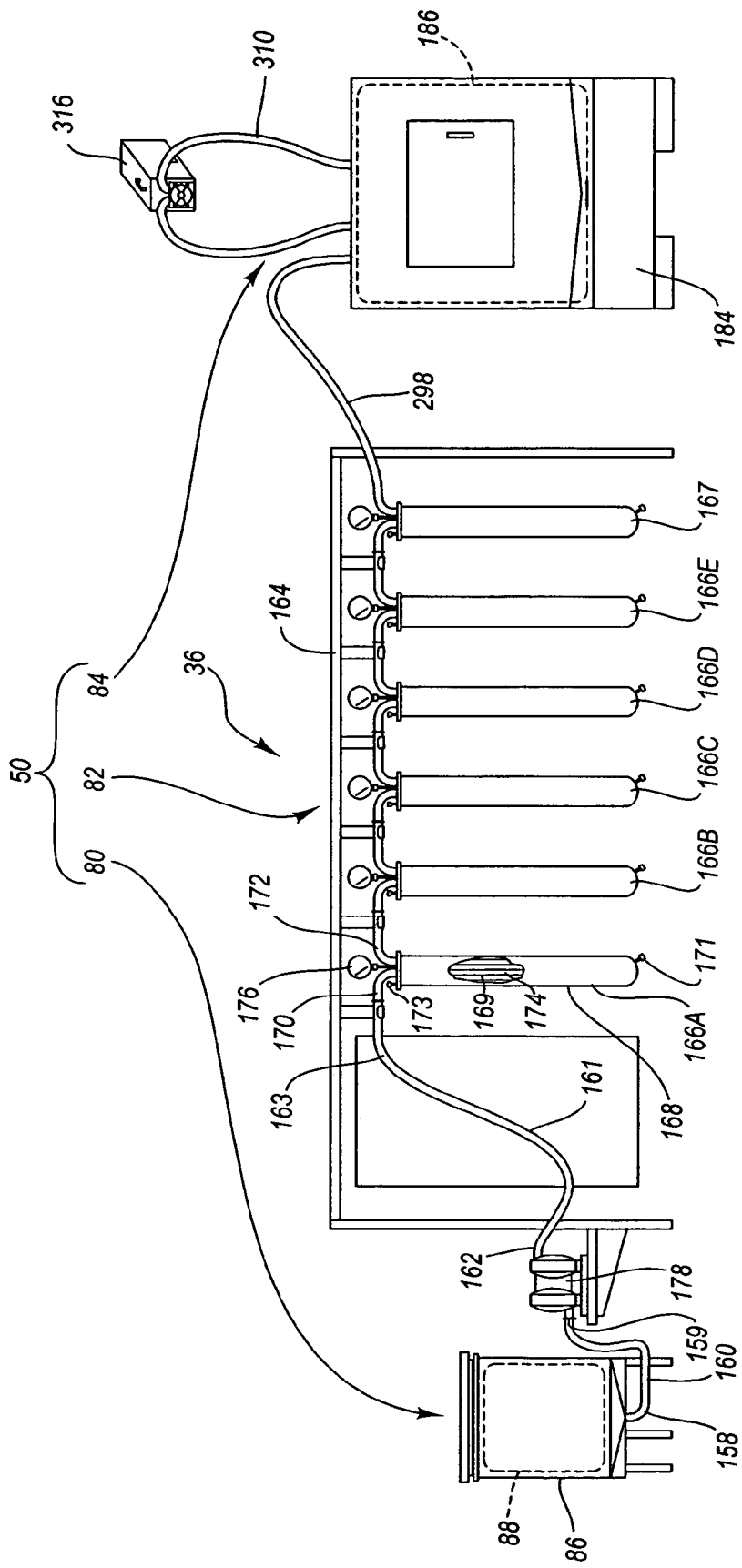
FIG. 4 is a front view of a filtration system disposed within the second housing shown in FIG. 3.
Figure 5:
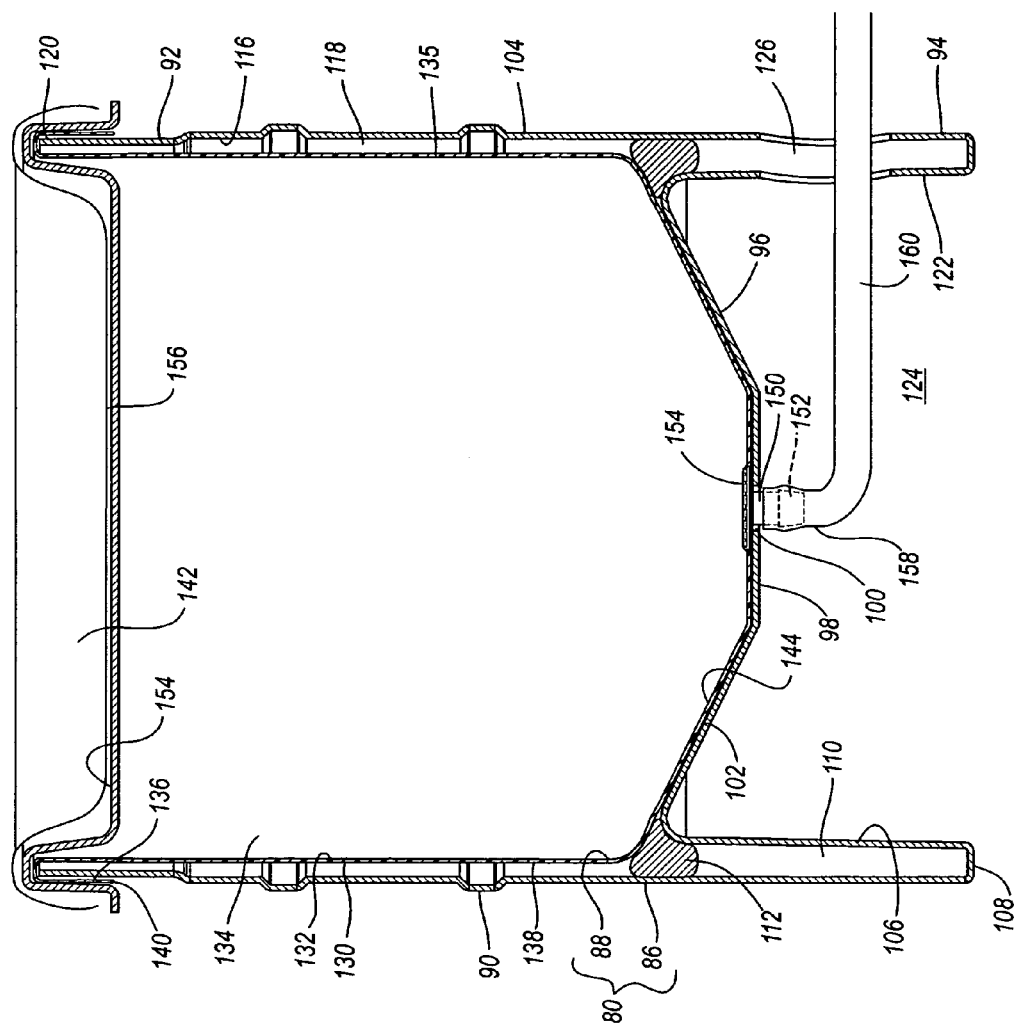
FIG. 5 is cross sectional side view of a fill container assembly of the filtration system shown in FIG. 4.

Turning to FIG. 4, filtration system 50 generally comprises a fill container assembly 80, a filter assembly 82, and a pooling container assembly 84. As depicted in FIG. 5, fill container assembly 80 comprises a rigid support container 86 having an open top, single-use fill bag 88 disposed therein. Support container 86 is disposed within filtration room 44 and can be secured to second housing 12 such as by straps or other conventional techniques so as to prevent shifting during transport. Support container 86 comprises a substantially cylindrical side wall 90 that extends from an upper end 92 to an opposing lower end 94. A floor 96 is formed inside of support container 86 at a position between upper end 92 and lower end 94. Floor 96 comprises a flat, circular base 98 having an aperture 100 extending therethough. A substantially frustoconical shoulder 102 encircles base 98 and extends from base 98 to side wall 90.

In the embodiment depicted side wall 90 comprises an outer wall 104 that extends between opposing ends 92 and 94 and an inner wall 106 that extends from shoulder 102 of floor 96 to lower end 94. An annular transition 108 connects outer wall 104 and inner wall 106 at lower end 94. Above transition 108, outer wall 104 and inner wall 106 are spaced apart so as to form an annular gap 110. An annular seal 112 is disposed within gap 110 so as to form a bridge between outer wall 104 and inner wall 106 at the location where inner wall 106 connects with shoulder 102 of floor 96. Seal 112 combines with shoulder 102 to form a portion of floor 96. In part, seal 112 functions to prevent fill bag 88 from sliding into gap 110 which could cause failure of fill bag 88.

In the embodiment depicted, support container 86 is molded so that outer wall 104, inner wall 106, transition 108, and floor 96 are all integrally formed as a single molded item. In alternative embodiments, inner wall 106 and seal 112 can be eliminated. This can be accomplished by integrally molding floor 96 directly to outer wall 104 or by having a discrete floor 96 that is connected to outer wall 104 such as by welding, fasteners, or the like.

Shoulder 102 of floor 96 is sloped so as to function in part as a funnel that directs all material toward aperture 100. In alternative embodiments, floor 96 can be flat, cupped, irregular, or other desired configurations.

Side wall 90 of support container 86 has an interior surface 116 disposed above floor 96. Interior surface 116 and floor 96 bound a first chamber 118 formed in upper end 92 of support container 86. First chamber 118 can be sized to have any desired volume. For example, first chamber 118 can be sized to hold 50 liters, 100 liters, 200 liters, or other desired volumes. In the present example, first chamber 118 is sized to hold approximately 100 liters. Upper end 92 of support container 86 terminates at an upper edge 120 that bounds an opening to first chamber 118. An optional annular lid can be removably disposed over upper edge 120 so as to selectively close the opening.

Side wall 90 also has an interior surface 122 formed below floor 96. Interior surface 122 and floor 96 bound a second chamber 124 disposed at lower end 94 of support container 86. An access port 126 extends through side wall 90 at lower end 94 of support container 86 so as to provide side access to second chamber 124. In alternative embodiments, the portion of side wall 90 extending below floor 96 can be replaced with one or more spaced apart legs or other supports that elevate floor 96 off of the floor.

In the embodiment depicted, support container 86 comprises a barrel molded from a polymeric material. In alternative embodiments, support container 86 can be comprised of metal, fiberglass, composites, or any other desired material. Furthermore, although support container 86 is shown as having a substantially cylindrical configuration, support container 86 can be substantially boxed shaped or have a transverse configuration that is polygonal, elliptical, irregular, or any other desired configuration.

Fill bag 88 is removably disposed within first chamber 118 of support container 86. Fill bag 88 comprises a flexible bag-like body 130 having an interior surface 132 that bound a compartment 134. More specifically, body 130 comprises a side wall 135 that, when body 130 is unfolded, has a substantially circular or polygonal transverse cross section that extends between a first end 136 and an opposing second end 138. First end 136 terminates at an open perimeter edge 140. Perimeter edge 140 bounds an mouth 142 to compartment 134. Second end 138 terminates at a bottom end wall 144.

Body 130 is comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet which comprises two or more layer of different material that are each separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. Still another example of a film that can be used in the Attane film which is likewise available from HyClone Laboratories, Inc. The Attane film is produced from three independent webs of blown film. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film). In yet other embodiments, body 130 can be made exclusively of the HyQ BM1 film or the HyQ BX6 film.

In one embodiment, the material is approved for direct contact with living cells and is capable of maintaining a solution sterile. In such an embodiment, the material can also be sterilizable such as by ionizing radiation. Other examples of materials that can be used are disclosed in U.S. Pat. No. 6,083,587 which issued on Jul. 4, 2000 and U.S. patent application Ser. No. 10/044,636, filed Oct. 19, 2001 which are hereby incorporated by specific reference.

In one embodiment, body 130 comprises a two-dimensional pillow style bag wherein two sheets of material are placed in overlapping relation and the two sheets are bounded together at their peripheries to form internal compartment 134. Alternatively, a single sheet of material can be folded over and seamed around the periphery to form internal compartment 134. In another embodiment, body 130 can be formed from a continuous tubular extrusion of polymeric material that is cut to length and one end seamed closed. In still other embodiments, body 130 can comprise a three-dimensional bag which not only has an annular side wall but also a two dimensional bottom end wall 144. The formation of three-dimension bags will be discussed below in greater detail.

It is appreciated that body 130 can be manufactured to have virtually any desired size, shape, and configuration. For example, body 130 can be formed having compartment 134 sized to hold 50 liters, 100 liters, 200 liters, or other desired amounts. In the present example, body 130 is sized to hold approximately 100 liters. During use, however, significantly less than 100 liters of serum is typically within body 130 at any given time, thereby avoiding any potential for spilling. Although body 130 can be any shape, in one embodiment body 130 is specifically configured to be complementary or substantially complementary to first chamber 118 of support container 86.

In any embodiment, however, it is desirable that when body 130 is received within first chamber 118, body 130 is uniformly supported by floor 96 and side wall 90 of container support container 86. Having at least generally uniform support of body 130 by support container 86 helps to preclude failure of body 130 by hydraulic forces applied to body 130 when filled with serum or other liquids.

Mounted on bottom end wall 144 of body 130 is a port 150. Port 150 comprises a barbed tubular stem 152 having a flange 154 outwardly projecting from an end thereof. During assembly, a hole is formed through body 130 and port 150 passed therethrough. Conventional welding or other sealing techniques are then used to seal flange 154 to body 130. It is appreciated that any number of ports can be formed on body 130 and that a variety of different types and sizes of ports can be used depending on the type of material to be dispensed into compartment 134 and how the material is to be dispensed therefrom.

Fill bag 88 is disposed within first chamber 118 of support container 86 so that stem 152 passes through aperture 100 on floor 96 of support container 86. A first end 158 of a first fluid line 160 is coupled with stem 158. First fluid line 160 passes out through access port 126 and couples with filter assembly 82 as will be discussed below in greater detail. Perimeter edge 140 of fill bag 88 is outwardly folded over the upper edge 120 of support container 86 so as to open mouth 142 of fill bag 88 and support fill bag 88 within support container 86. Next, an annular screen tray 154 is seated over upper edge 120 of support container 86 so as to span across open mouth 142 of fill bag 88. Finally, an initial filter 156 is laid over screen tray 154. Initial filter 156 is typically comprised of cheese cloth having a desired porosity. Other types and sizes of filters can also be used.

As depicted in FIGS. 3 and 4, filter assembly 82 comprises a filter rack 164 rigidly mounted to back wall 16 of second housing 12 within filter room 44. As depicted in FIG. 4, plurality of disposable filters 166A-E and a final filter 167 are mounted on rack 164 and fluid connected together in series so as to form a filter train. As will be discussed below in greater detail, final filter 167 forms a portion of pooling container assembly 84. If desired, to avoid down time in changing filters, two or more filter trains can be formed in parallel. As one or more filters of one filter train are being changed, the fluid can be routed through the second filter train.

Each filter 166 and 167 comprises a capsule 168 bounding a compartment 169. An inlet port 170 and an outlet port 172 communicate with compartment 169. Disposed within compartment 169 is a filter membrane 174. Filter membrane 174 is disposed such that fluid entering through inlet port 170 must pass through filter membrane 174 before exiting through outlet port 172. A bleed valve 173 is mounted on the top of capsule 168 to enable the removal of air from compartment 169. Bleed valve 173 communicates with compartment 169 on the inlet side of filter membrane 174. Similarly, a drain valve 171 is mounted on the bottom of capsule 168 so as to communicate with compartment 169 on the inlet side of filter membrane 174. As discussed below in greater detail, drain valve 171 is used to remove residual serum from capsule 168.

The number, type, and size of filters 166A-E depends on the amount, type, and speed at which the material is to be processed. For example, in one embodiment the filter train can comprise two prefilters having a filter membrane 174 with porosity in a range between about 0.2 μm to about 10 μm followed by three sterilizing filters each having a filter membrane 174 with a porosity of 0.1 μm. If desired, filters having a porosity down to 0.04 μm or smaller can be used to remove viruses. In other embodiment, only one or more filters may be required.

Filters which can be used in the present invention are available from the Pall Corporation. Examples of prefilters from the Pall Corporation that can be used include the Profile prefilter which is a polypropylene depth filter with tapered pore structure and a pore size of 5 μm; the Profile Star which is a polypropylene filter with a star shaped pleat structure and a pore size of 5 μm; the Ultipor GF Plus prefilter which is a bonded glass fiber filter with positive Zeta potential and a pore size of 20/2 μm; and the Preflow UUA prefilter which is a resin bonded glass fiber filter having a pore size of 0.2 μm.

The three final filters are designed for mycoplasma removal. Examples of such final filters available from the Pall Corporation include the Posidyne NGZ01 filter and the Fluorodyne II DJLP filter each having a pore size of 0.1 μm. The Posidyne NGZ01 filter incorporates charge-modified Nylon 6,6 membranes, which exhibit a positively charged Zeta potential in aqueous solutions. A positively charged filter provides adsorption-enhanced retention of particles smaller than the filter rating. The Posidyne NGZ01 filter provides high protein recovery from sera and most protein solutions, and has a Acholeplasma laidlawii mycoplasma titer reduction rated at >$10^6$/cartridge.

The Fluorodyne II DJLP filter has two layers of PVDF membrane with a built-in 0.2 micron prefilter layer and a final 0.1 micron layer. The DJLP filter has a flow rate comparable to the flow rate of traditional 0.2 micron filter, which allows for economical 0.1 micron filtration.

Filters 166 and 167 come in a variety of different sizes such as 10 inch, 20 inch, 30 inch or the like. Increasing the length of filters 166 and 167 increases the surface area of filter membrane 174, thereby increasing flow rate and the amount of material that can be processed. In one embodiment each capsule 168 is translucent. This feature allows visual assurance that compartments 169 have been properly bled of air so that complete utilization of the filter membrane is achieved. Completion of filtration can also be confirmed by observing fluid in the filters.

A pressure gauge 176 is mounted on each capsule 168 so as to measure the pressure of the fluid within compartment 169 prior to passing through the corresponding filter membrane 174. The pressure drop between two adjacent pressure gauges 176 is a result of the fluid having to pass through the filter member 174 between the two pressure gauges 176. As filter membrane 174 becomes increasingly occluded by filtering out unwanted material, the pressure drop increases. Accordingly, by continually monitoring the pressure differential between pressure gauges 176, an operator can select the optimal time to replace clogged filters.

The replacement procedure can comprise shutting down the filtration process and then replacing the clogged filter. Alternatively, it is appreciated that parallel routing paths can be formed for one or more of the filters. Accordingly, as a filter becomes clogged, one or more valves are activated so that the fluid is routed around the clogged filter while the clogged filter is being replaced. This configuration eliminates the need to shut down the filtering process. During most operations, it is typically only necessary to replace the first filter 166A, if any.

As mentioned above, in one embodiment filters 166 and 167 are completely disposable. In such embodiments, filter membrane 174 is typically sealed within a polymeric capsule 168. In an alternative embodiment, capsule 168 can comprise a stainless steel reusable housing in which filter membrane 174 is removably disposed. Of course, this latter embodiment requires cleansing of the housing between each use.

As also depicted in FIG. 4, first fluid line 160 has first end 158 fluid coupled with fill bag 88 as discussed above and a second end 159 that is fluid coupled to an inlet side of a pump 178. A second fluid line 161 has a first end 162 fluid coupled to an outlet side of pump 178 and a second end 163 fluid coupled to inlet port 170 of first filter 166A. Pump 178 draws the fluid from fill bag 88 and passes it through filters 166 and 167. In the depicted embodiment pump 178 comprises a conventional diaphragm pump having an air regulator. By adjusting the air regulator, pump 178 can be set to operate so as not to exceed a defined pressure. That is, as filters 166 and 167 become increasingly occluded, the fluid pressure increases. The pressure, however, needs to stay below a predefined level to prevent failure of the system, i.e., rupturing of a fluid line or seal. Although other pressures can be used, in one embodiment pump 178 is set not to produce a fluid pressure in excess of about 60 psi (41 N/m$^2$).

Because the unfiltered serum actually passes through pump 178, pump 178 is one of the few items that must be cleaned between the processing of each separate batch. In an alternative embodiment, pump 178 can comprise a peristaltic pump. In this embodiment, first fluid line 160 and second fluid line 161 comprise a single integral line that passes through the peristaltic pump. Because the peristaltic pump does not actually contact the unfiltered serum but merely constricts the fluid line to advance the serum therein, the peristaltic does not need to be cleaned between different batches. It is sufficient merely to replace the fluid line. The downside with using a peristaltic pump, however, is that they typically have a lower flow rate and are typically not configured so as to prevent exceeding a desired fluid pressure. Other conventional pumps can also be used.

Figure 6:
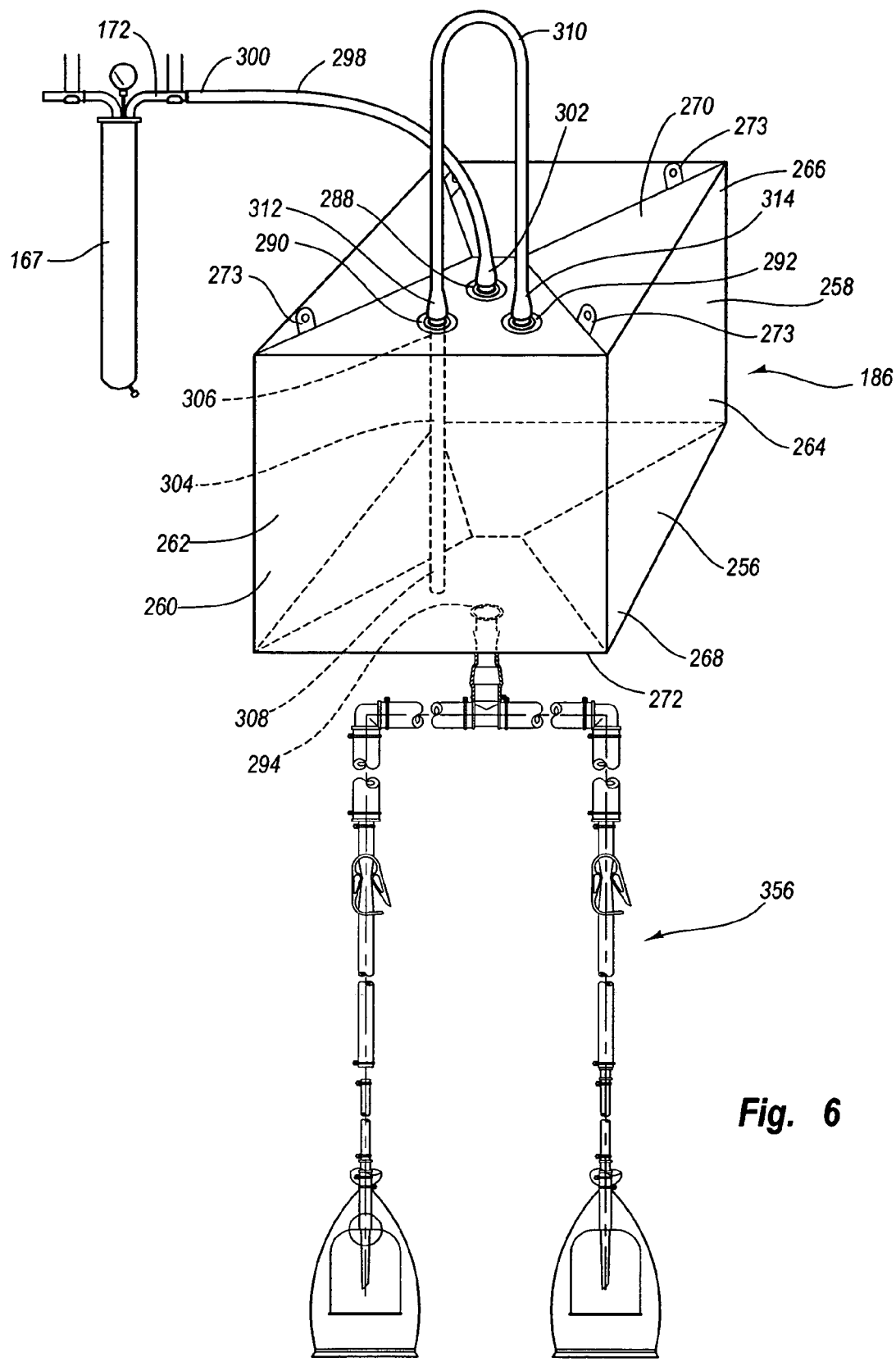
FIG. 6 is a perspective view of a pooling bag assembly of the filtration system shown in FIG. 4.
Figure 11:
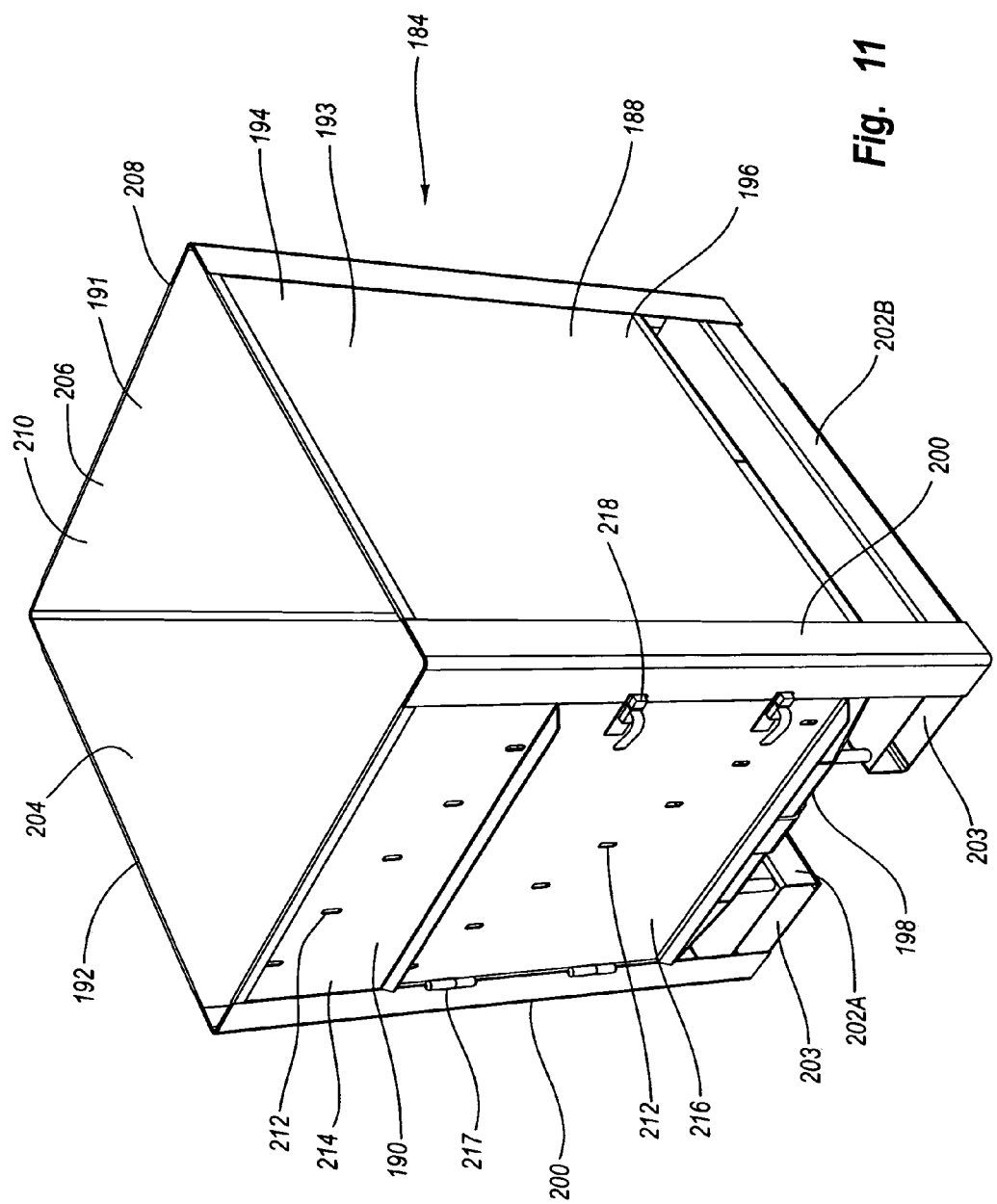
FIG. 11 is a perspective view of a support bin of the filtration system shown in FIG. 4.

Pooling container assembly 84 as depicted in FIG. 4 comprises a pooling bag assembly 186 as depicted in FIG. 6 and a rigid support bin 184 as depicted in FIG. 11. Turning to FIG. 6, pooling bag assembly 186 comprises a pooling bag 256. Pooling bag 256 comprises a flexible body 258 having an interior surface 260 that bounds a chamber 262. Although chamber 262 can be any desired volume, in the present example, chamber 262 is configured to hold a volume of at least 1,000 liters so that the entire batch of serum can simultaneously be held within chamber 262. Body 258 is comprised of a flexible, water impermeable material such as the various polymeric sheets as previously discussed with regard to fill bag 88.

In contrast to fill bag 88, however, which has an open mouth, body 258 of pooling bag 256 is sealed closed. As such, it is desirable that body 258 be comprised of a gas barrier layer that prevents the migration of contaminating gases into chamber 262. Examples of materials that include a gas barrier layer include the HyQ CX5-14 cast film and the Attane type films, as previously discussed. A gas barrier layer is desirable in body 258 to maintain sterility in the filtered serum downstream of final filter 167 and to keep the filtered serum free of any gas phase. When the volume of fill bag 88 is smaller than the volume of pooling bag 256, the serum spends less time (and is typically colder) in fill bag 88 than in pooling bag 256.

Furthermore, although body 258 can comprise a two-dimensional pillow style bag, in the depicted embodiment, body 258 comprises a three-dimensional bag. More specifically, body 258 comprises an encircling side wall 264 that, when body 258 is unfolded, has a substantially circular or polygonal transverse cross section that extends between a first end 266 and an opposing second end 268. First end 266 terminates at a two dimensional top end wall 270 while bottom end 268 terminates at a two dimensional bottom end wall 272. A plurality of spaced apart loops 273 are formed on top end wall 270. Loops 273 enable pooling bag 256 to be lifted and supported, if desired, during filling of filtered serum into pooling bag 256.

Figure 7:
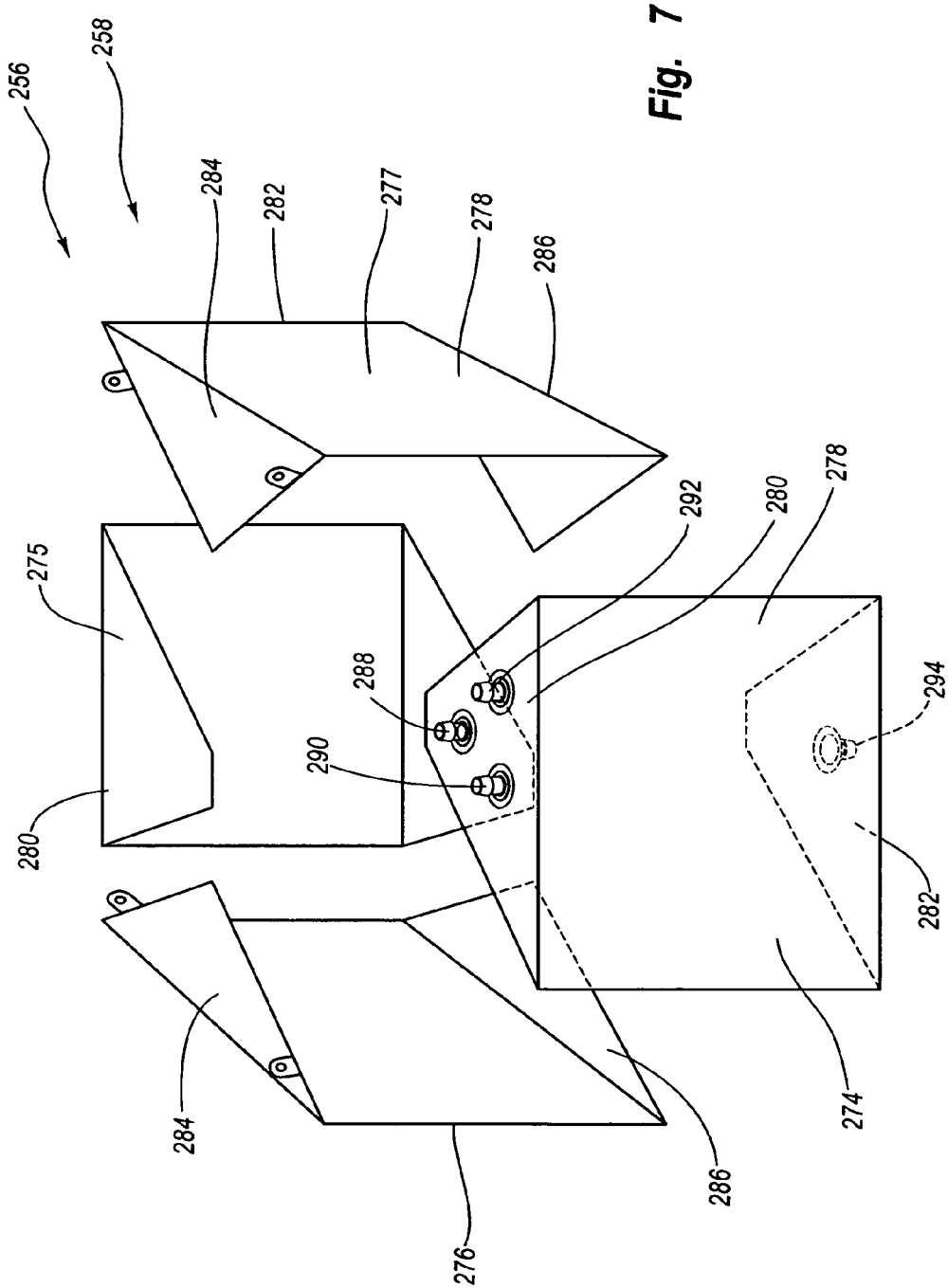
FIG. 7 is a partially exploded perspective view of a pooling bag of the pooling bag assembly shown in FIG. 6.

Turning to FIG. 7, three dimensional body 258 is comprised of four discrete panels, i.e., a front panel 274, a back panel 275, a first side panel 276, and a second side panel 277. Each panel 274-277 has a substantially square or rectangular central portion 278. Front panel 274 and back panel 275 each have a first end portion 280 and a second end portion 282 projecting from opposing ends of central portion 278. Each of end portions 280 and 282 have a trapezoidal configuration with opposing tapered sides. Each of side panels 276 and 277 has a triangular first end portion 284 and an opposing triangular second end portion 286 at the opposing ends of central portion 278. As depicted in FIG. 6, corresponding perimeter edges of each panel 274-277 are seamed together so as to form body 258 having a substantially box shaped configuration. In this assembled configuration, each of panels 274-277 is folded along the intersection of the central portion and each of the end portions such that end portions combine to form top end wall 270 and bottom end wall 272.

Panels 274-277 are seamed together using methods known in the art such as heat energies, RF energies, sonics, other sealing energies, adhesives, or other conventional processes. It is appreciated that by altering the size and configuration of some or all of panels 274-277, body 258 can be formed having a variety of different sizes and configurations. The size and configuration of body 258 can also be altered by varying the number of panels used to make body 258.

In still other embodiments, it is appreciated that body 80 can be formed by initially extruding or otherwise forming a polymeric sheet in the form of a continuous tube. Each end of the tube can then be folded like the end of paper bag and then seamed closed so as to form a three dimension body. In still another embodiment, a length of tube can be laid flat so as to form two opposing folded edges. The two folded edges are then inverted inward so as to form a pleat on each side. The opposing end of the tube are then seamed closed. Finally, an angled seam is formed across each corner so as to form a three dimensional bag when unfolded.

It is appreciated that the above techniques can be mixed and matched with one or more polymeric sheets and that there are still a variety of other ways in which body 258 can be formed having a two or three dimensional configuration. Further disclosure with regard to one method of manufacturing three-dimensional bags is disclosed in U.S. patent application Ser. No. 09/813,351, filed on Mar. 19, 2001 of which the drawings and Detailed Description are hereby incorporated by specific reference.

Pooling bag 256 further comprises a plurality of tubular ports mounted on body 258 so as to communicate with chamber 262. As depicted in FIG. 7, a filter port 288 and two circulation ports 290 and 292 are mounted on first end portion 280 of front panel 274 of body 258. A single outlet port 294 is formed on second end portion 282 of front panel 274 of body 258. Pooling bag assembly 186 also comprises various fluid. lines being fluid coupled with the above referenced ports. For example, as depicted in FIG. 6, a third fluid line 298 has a first end 300 fluid coupled with outlet port 172 of final filter 167 and an opposing second end 302 fluid coupled with filter port 288.

Likewise, a dip tube 304 is disposed within chamber 262 of pooling bag 256 and has a first end 306 disposed at circulation port 290 and a second end 308 disposed toward bottom end wall 272 of pooling bag 256. In turn, a circulation line 310 has a first end 312 fluid coupled with circulation port 290 and a second end 314 fluid coupled with circulation port 292. As depicted in FIGS. 4 and 6, a pump 316 is coupled with circulation line 310. Pump 316 functions to draw filtered serum or other fluid located at the bottom of pooling bag 256 up through dip tube 304, through circulation line 310 and then back into the top of pooling bag 256 though circulation port 292. The operation of pump 316 thus functions to mix the filtered serum within pooling bag 256 so that the filtered serum becomes and remains homogenous. Although any type of pump can be used, in one embodiment pump 316 comprises a peristaltic pump. Because the peristaltic pump does not directly contact the fluid, the peristaltic pump can be repeatedly used for different batches without cleaning or risk of contamination.

Figure 8:
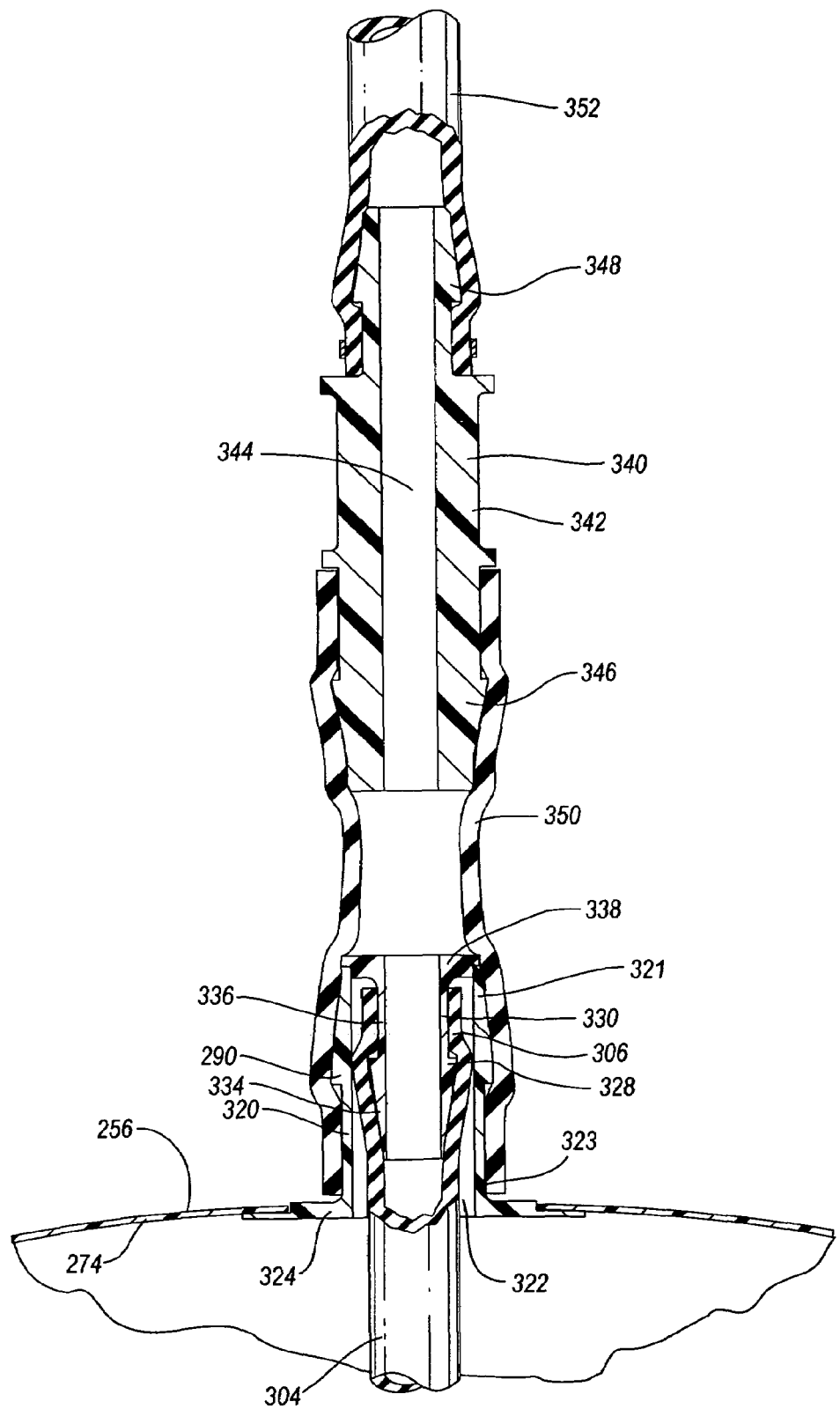
FIG. 8 is a cross sectional side view showing a connection of a dip tube to the pooling bag shown in FIG. 6.

Depicted in FIG. 8 is one embodiment of how dip tube 304 is mounted to pooling bag 256. Specifically, circulation port 290 comprises a tubular, barbed stem 320 that bounds a channel 322 extending therethrough. Stem 320 has a first end 321 and an opposing second end 323. A flange 324 is mounted on second end 323 of stem 320 and is secured to front panel 274 of pooling bag 256.

A diptube connector 328 is partially disposed within circulation port 290. Diptube connector 328 comprises a tubular, barbed stem 330 having a first end 334 and an opposing second end 336. An annular flange 338 encircles and outwardly projects from second end 336 of stem 330. Flange 338 has a maximum diameter that is larger than or equal to the first end 321 of circulation port 290. During assembly, first end 334 of diptube connector 328 is secured by frictional engagement within first end 306 of dip tube 304. Second end 308 of dip tube 304 is then advanced through circulation port 290 until flange 338 of diptube connector 328 seats on first end 321 of circulation port 290.

To enable diptube connector 328 to fit within circulation port 290, circulation port 290 is typically made of an increased size. In one embodiment, an adapter 340 is used to reduce the size of the tube that extends from circulation port 290. Adapter 340 comprises a tubular body 342 that bounds a channel extending between a barbed first end 346 and an opposing barbed second end 348. First end 346 of adapter 340 has a configuration and size similar to first end 321 of circulation port 290. A transition tube 350 is fluid coupled with and extends between first end 321 of circulation port 290 and first end 346 of adapter 340. In contrast, second end 348 of adapter 340 is smaller than first end 346 and thus is sized to fit within a tube 352 that is smaller than transition tube 350.

In one embodiment, circulation ports 290 and 292 can be the same size and circulation line 310 can have a constant size extending therebetween. In an alternative embodiment, circulation port 292 can be smaller than circulation port 290. In this embodiment, circulation line 310 comprises transition tube 350, adapter 340, and tube 352. Further disclosure with regard to diptube connector 328 and adapter 340 is provided in U.S. Pat. No. 6,086,574, issued Jul. 11, 2000, which is incorporated herein by specific reference.

Figure 9:
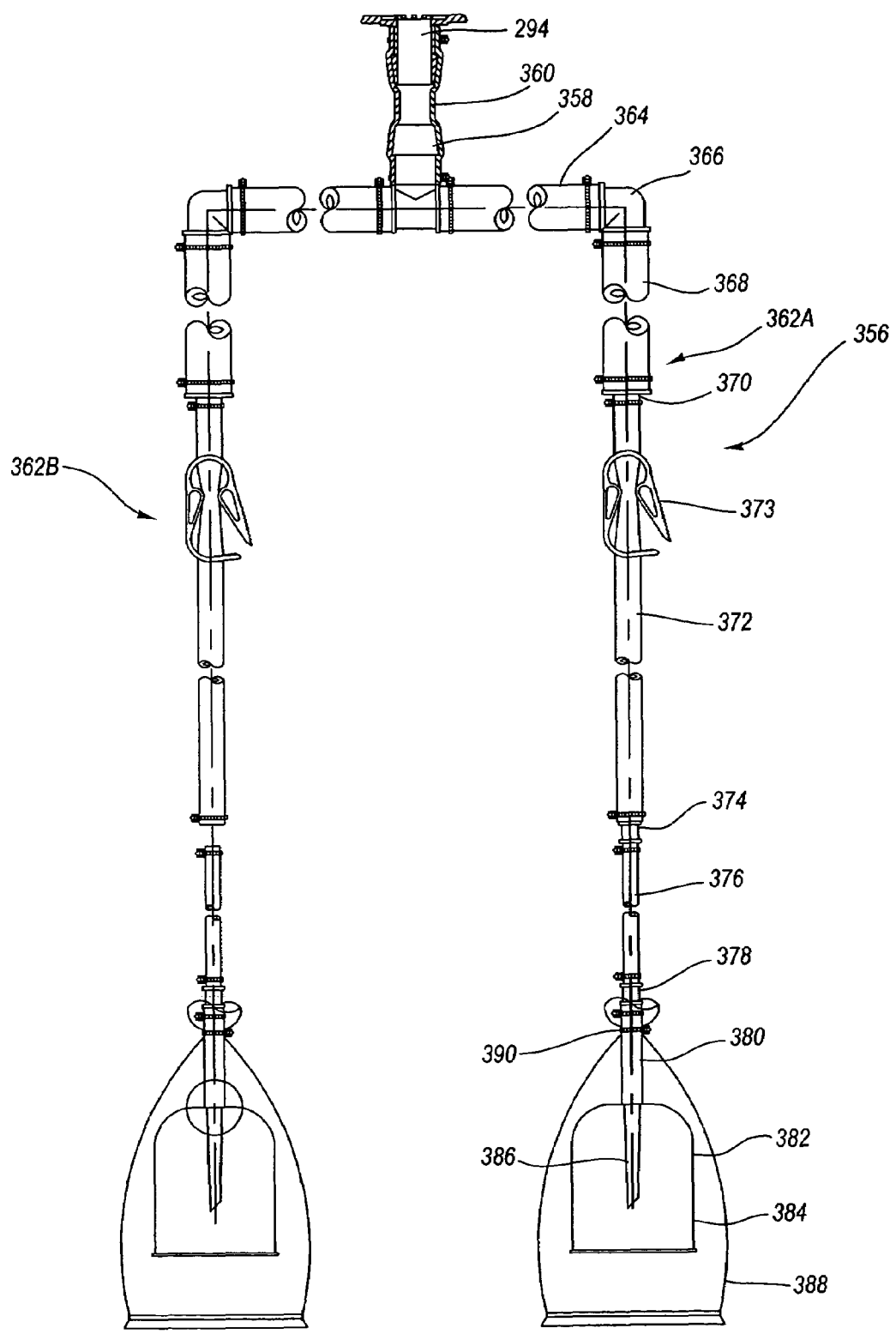
FIG. 9 is a partial cross sectional top plan view of a fill line assembly of the pooling bag assembly shown in FIG. 6.

Finally, as depicted in FIG. 6, pooling bag assembly 186 also includes a fill line assembly 356 coupled with outlet port 294. As depicted in FIG. 9, fill line assembly 356 comprises a tee connect 358 fluid coupled with outlet port 294 by way of a flexible transition tube 360. In one embodiment transition tube 360 is comprised of silicone tubing having a inside diameter (ID) of 0.875 inches (2.22 cm). Fluid coupled to the two remaining ports of tee connect 358 are two fill lines 362A and B. As fill lines 362A and B are identical, only one of the fill lines will be discussed herein.

Fill line 362A comprises a flexible tube 364 extending from tee connector 358 to an elbow connector 366. A flexible tube 368 extends from elbow connector 366 to a first reducing coupling 370. A flexible tube 372 extends from first reducing coupling 370 to a second reducing coupling 374. Flexible tube 372 has an ID of 0.375 inches (0.95 cm). A hose clamp 373 is mounted on tube 372 so that the flow of fluid through tube 372 can be selectively stopped. A flexible tube 376 extends from second reducing coupling 374 to a third coupling 378. Tube 376 has an ID of 0.312 inches (0.79 cm). A flexible tube 380 extends from third coupling 378 to a filling bell 382. Tube 380 has an ID of 0.375 inches (0.95 cm). Filling bell 382 comprises a shroud 384 having a nozzle 386 mounted thereon so that the free end of nozzle 386 is disposed within shroud 384. Nozzle 386 also includes a tubular stem (not shown) that extends outside of shroud 384 and is coupled with tube 380. Finally, filling bell 382 is positioned within a polymeric bag 388 which is sealed around tube 380 by a cable tie 390. Bag 388 thus seals nozzle 386 in a closed environment.

In one embodiment, tubes 360, 364, 368, 372, and 376 are all comprised of silicone which has desired properties with regard to durability and flexibility. The tubes start large to optimize flow in each fill line but are subsequently reduced. As discussed below in greater detail, the size reduction is made to optimize pumping and filling parameters. Filling bell 382 is molded as a single integral unit that is comprised of polycarbonate. Tube 380 is comprised of a medical grade PVC. By forming tube 380 out of PVC, as opposed to silicone, tube 380 can be secured to filling bell 382 using an adhesive. In alternative embodiments, the tubes can be made of different materials and can have different sizes. Furthermore, in other embodiments, fill line assembly 356 can comprise one fill line or three or more fill lines.

Figure 10:
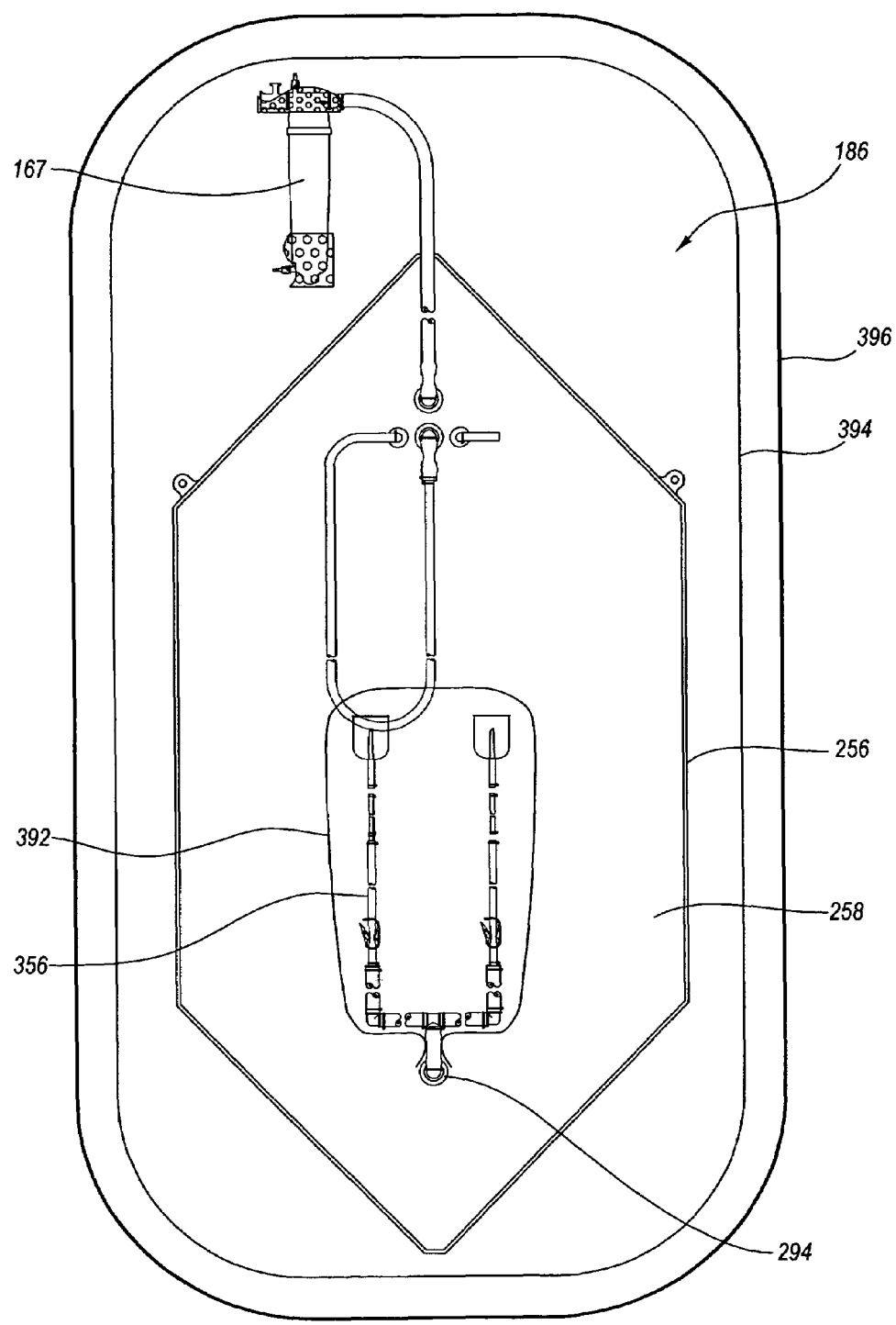
FIG. 10 is a top plan view of the pooling bag assembly shown in FIG. 6 in a collapsed state and sealed within double bags.

In one embodiment, pooling bag assembly 186, including final filter 167, is preassembled as a discrete unit. In this preassembled state, as shown in FIG. 10, pooling bag 256 is folded and collapsed with substantially all of the air removed therefrom. Fill line assembly 356 is coil and placed within a polymeric bag 392 which is tied closed around or adjacent to outlet port 294. The entire pooling bag assembly 186, including final filter 167, is then sealed within a first packaging bag 394 which is then sealed within a second packaging bag 396, each bag 394 and 396 being heat sealed closed. The entire pooling bag assembly 186 with the packaging bags is then gamma-irradiated so as to sterilize pooling bag assembly 186 and any air trapped therein.

Figure 12:
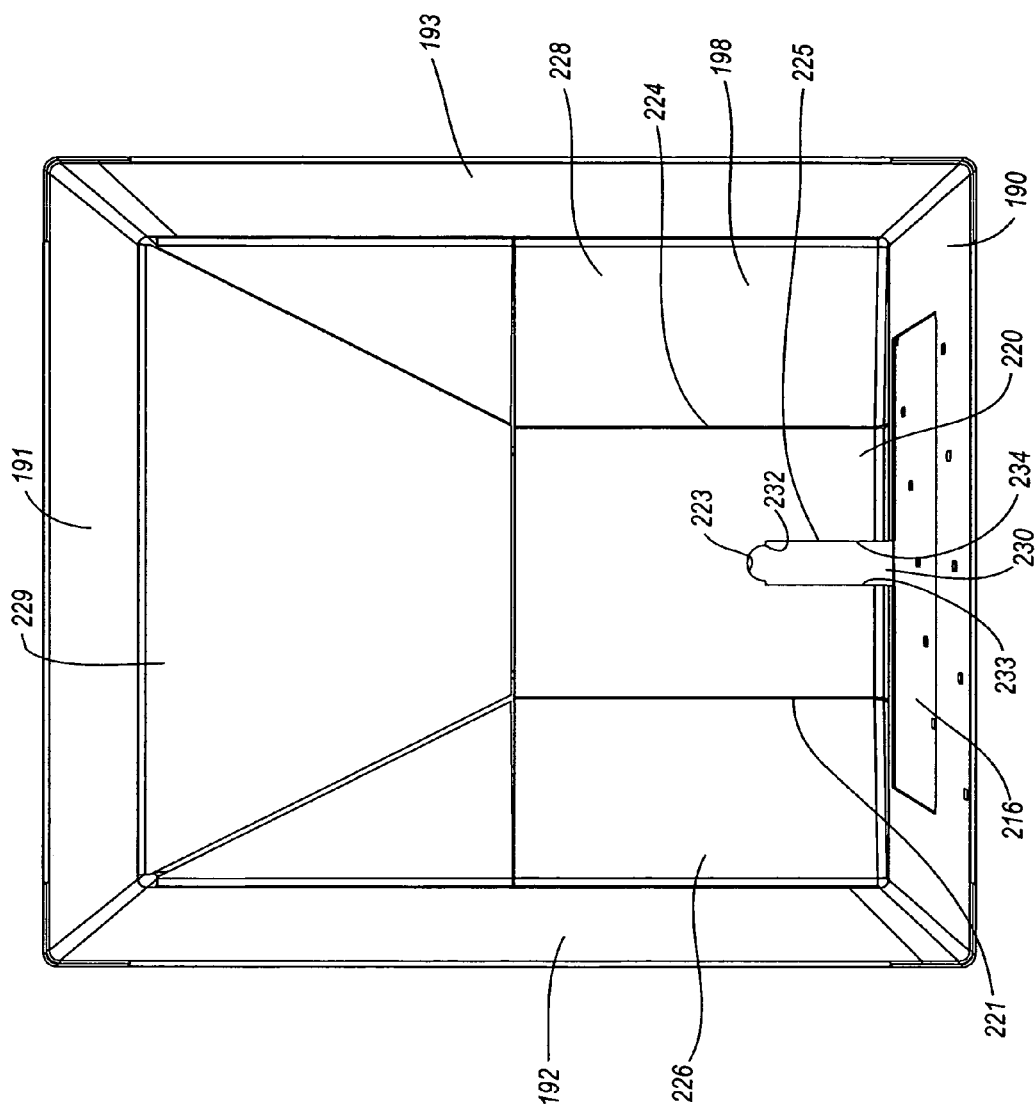
FIG. 12 is a partially disassembled top plan view of the support bin shown in FIG. 11.

Turning to FIG. 11, support bin 184 comprises an encircling side wall 188 that includes a front panel 190, an opposing back panel 191, and a pair of spaced apart side panels 192 and 193 extending therebetween. Each of panels 190-193 has an upper end 194 and an opposing lower end 196. Extending between each of panels 190-193 at lower end 196 is a floor 198 (FIG. 12).

A support leg 200 is mounted at the intersection of each of panels 190-193 with each support leg 200 extending below floor 198. As a result, legs 200 elevate floor 198 off the ground or support surface so as to provide access to the bottom surface of floor 198. Any structure that enables access to the bottom surface of floor 198 can also be used to replace legs 200. A pair of spaced apart fork lift channels 202A and B extend between two adjacent legs 200 along side panels 192 and 193. Each channel 202 bounds an opening 203 adapted to receive a fork from a fork lift. A motorized or hand operated fork lift can thus be used to easily lift and move support bin 184. Support bin 184 is periodically moved so as to allow cleaning therebehind.

Support bin 184 has an interior surface 204 which bounds a chamber 206. Upper end 194 of side wall 188 terminates at an upper edge 208. Upper edge 208 bounds an opening 210 which communicates with chamber 206. A lid can be used to selectively cover opening 210 to chamber 206. Horizontally and vertically staggered slots 212 extend through front panel 190 and allow visual determination of a fluid level within chamber 206. Chamber 206 can be any desired volume. By way of example, support bin 184 can be formed having chamber 206 with a volume of 500 liters, 1,000 liters, 1,500 liters or other desired volumes. In the present example, chamber 206 is configured to hold a volume of at least 1,000 liters.

Front panel 190 comprises a fixed panel 214 and a door 216. Fixed panel 214 bounds a doorway 219 (FIG. 13) which is selectively opened and closed by door 216. Specifically, door 216 is mounted to fixed panel 214 by hinges 217. Latches 218 mounted on the opposing side of door 216 selectively lock door 216 to fixed panel 214. As will be discussed below in greater detail, opening of door 216 enables easy access to chamber 206 and floor 198 of support bin 184 through doorway 219.

Support bin 184 can be comprised of metal, such as stainless steel, fiberglass, composites, plastic, or any other desired material. Furthermore, although support bin 184 is shown as having a substantially box shaped configuration, support bin 184 can be any desired configuration or have a transverse configuration that is polygonal, elliptical, irregular, or any other desired configuration.

Figure 13:
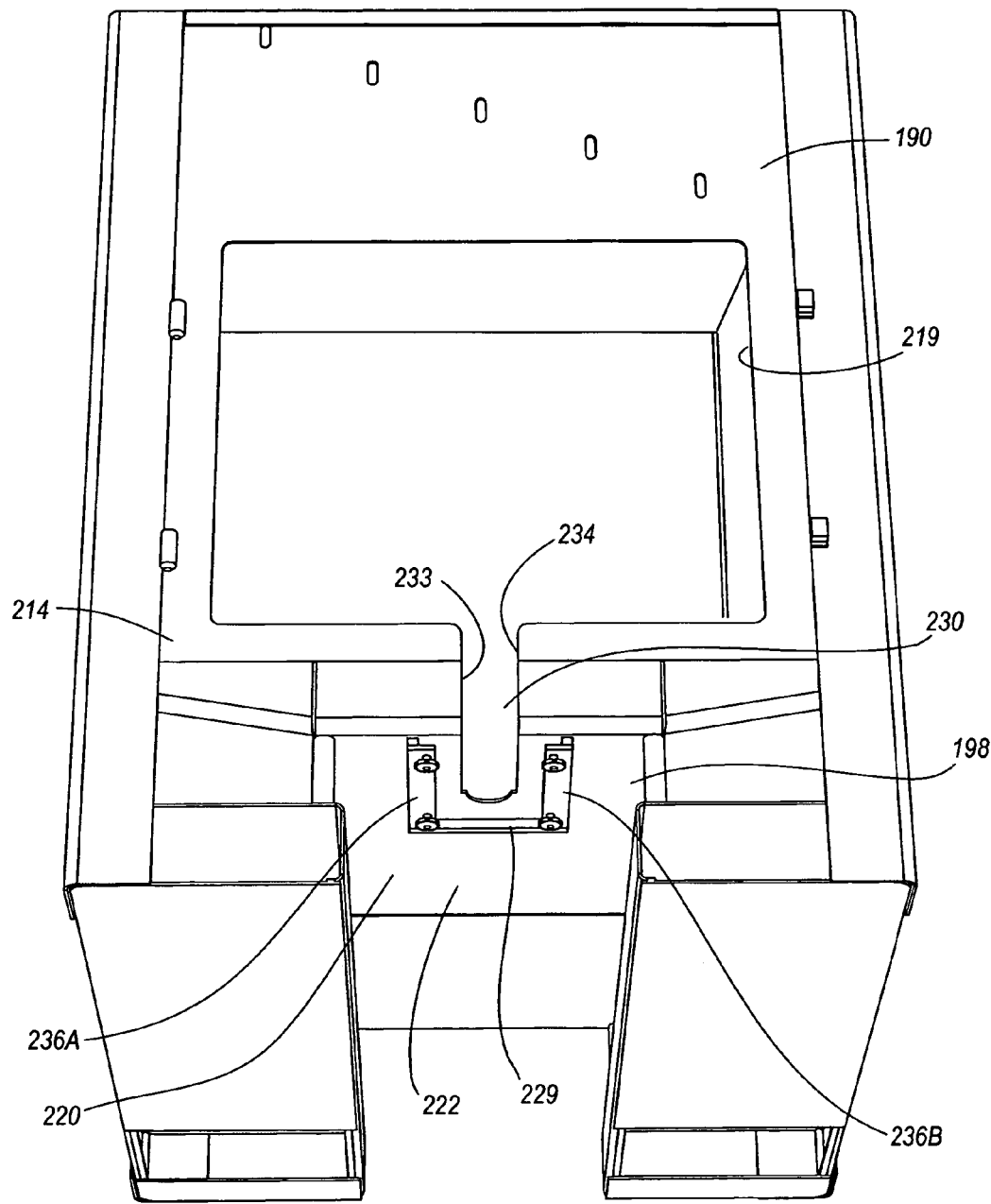
FIG. 13 is a partially disassembled bottom perspective view of the support bin shown in FIG. 11.

As depicted in FIGS. 12 and 13 (FIG. 13 being shown without door 216), floor 198 comprises a substantially flat base floor 220 having a top surface 221 and an opposing bottom surface 222. Base floor 220 is centrally disposed along front panel 190 and projects from front panel 190 toward back panel 191. Base floor 220 has an outer edge 224 and an inner edge 225. Floor 198 further comprises a first side floor 226 that downwardly slopes from side panel 192 to base floor 220, a second side floor 228 that downwardly slopes from side panel 193 to base floor 220, and a back floor 229 that downwardly slopes from back panel 191 to base floor 220. As a result, floor sections 226-228 are sloped to direct or funnel material to base floor 220. In an alternative embodiment, all of floor 198 can be substantially flat.

Inner edge 225 of base floor 220 bounds slot 230 which extends through base floor 220. Inner edge 225 includes a back edge 232, an opposing side edges 233 and 234. A semi-circular notch 223 is formed on back edge 232. Depicted in FIG. 13, opposing side edges 233, 234 and slot 230 also extend along fixed panel 214 of front panel 198 so as to intersect with doorway 219. As such, slot 230 has a substantially L-shaped configuration.

Figure 14:
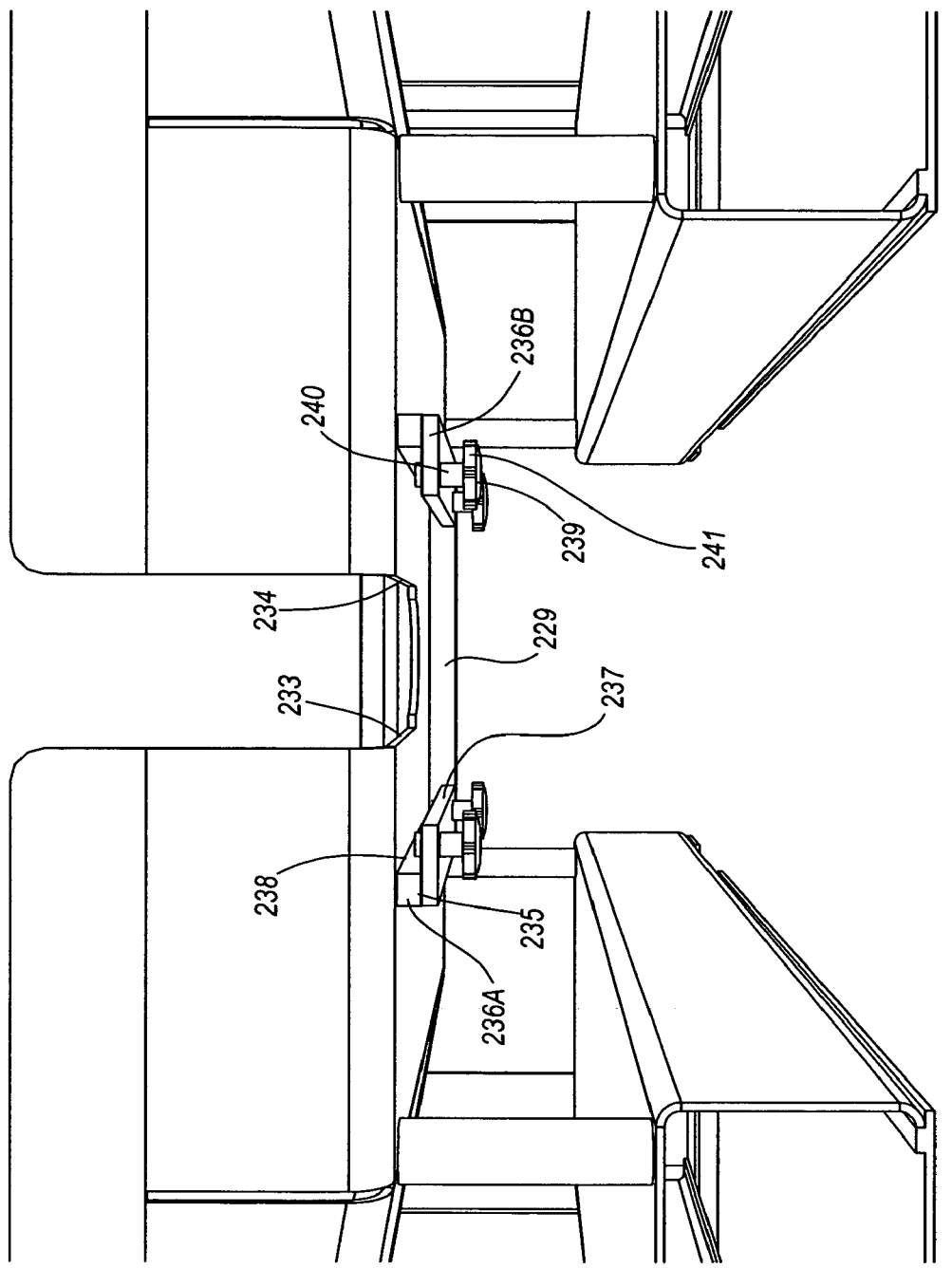
FIG. 14 is an elevated front view of a bracket shown in FIG. 13.

Depicted in FIGS. 13 and 14, mounted on bottom surface 222 of base floor 220 along side edges 233 and 234 are bracket assemblies 236A and B. Each bracket assembly 236 includes a flat elongated spacer 235 that is disposed directly on bottom surface 222 of base floor 220 but at a distance back from side edge 233 and 234. A stop plate 229 extends between spacers 235 at a distance back from back edge 232. Mounted on top of spacer 235 is an elongated substantially flat slide rail 237. Slide rail 237 extends along spacer 235 but also outwardly projects therefrom so as to freely project out toward side edge 233 and 234. As a result, a channel 238 is formed between slide rail 237 and base floor 220 along side edges 233 and 234 of base floor 220.

Spacer 235 and slide rail 237 can each comprise multiple discrete members or can each be a single integral member. Furthermore, spacer 235 and slide rail 237 can be formed as a combined integral member. Bolts, welding, or other types of fasteners can be used to secure spacer 235 and slide rail 237 to base floor 220. A plurality of securing fasteners 239 each include a threaded shaft 240 having a knob 241 mounted on an end thereof. For reasons as will be discussed below in greater detail, each shaft 240 threadedly engages with a corresponding slide rail 237 and passes therethrough so as to communicate with a corresponding channel 238.

Figure 15:
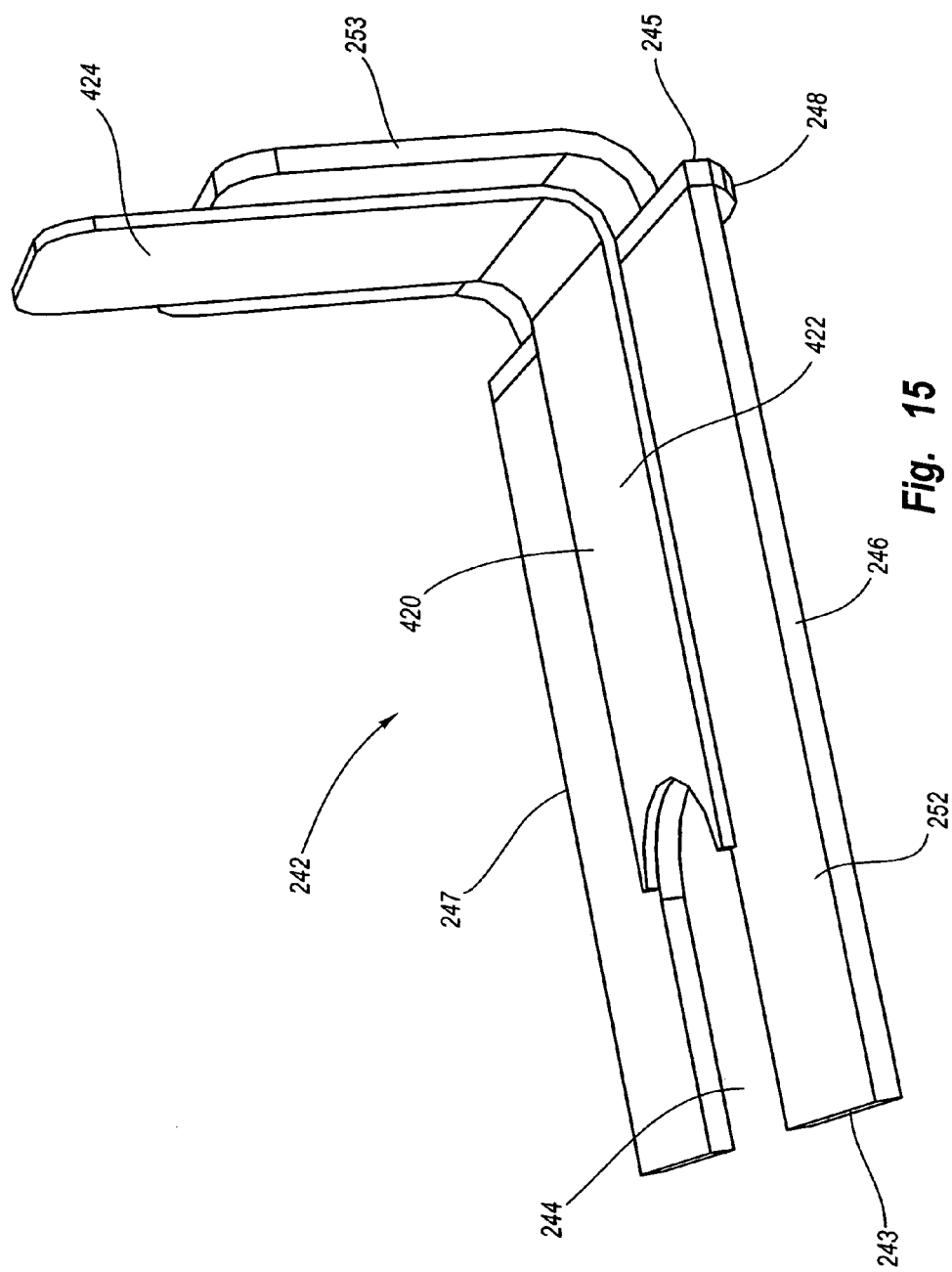
FIG. 15 is a perspective view of a retention plate of the support bin shown in FIG. 11.

Depicted in FIG. 15, support bin 184 also comprises a substantially L-shaped retention plate 242. Retention plate 242 comprises base plate 252 having a riser 253 upwardly projecting therefrom. Specifically, base plate 252 has a front edge 243, a back edge 245 and opposing side edges 246 and 247. A rounded notch 244 is formed on front edge 243 while a handle 248 downwardly projects from back edge 245. Riser 253 upwardly projects from back edge 245. A substantially L-shaped overlay 420 is mounted on base plate 252 and riser 253. Overlay 420 includes a base section 422 which extends on base plate 252 from notch 244 to riser 253. Overlay 420 also includes a tongue 424 which extends along riser 253 and then freely projects above riser 253. Overlay 420 has a width substantially equal to the width of slot 230 such that overlay 420 can be received within slot 230.

Figure 16:
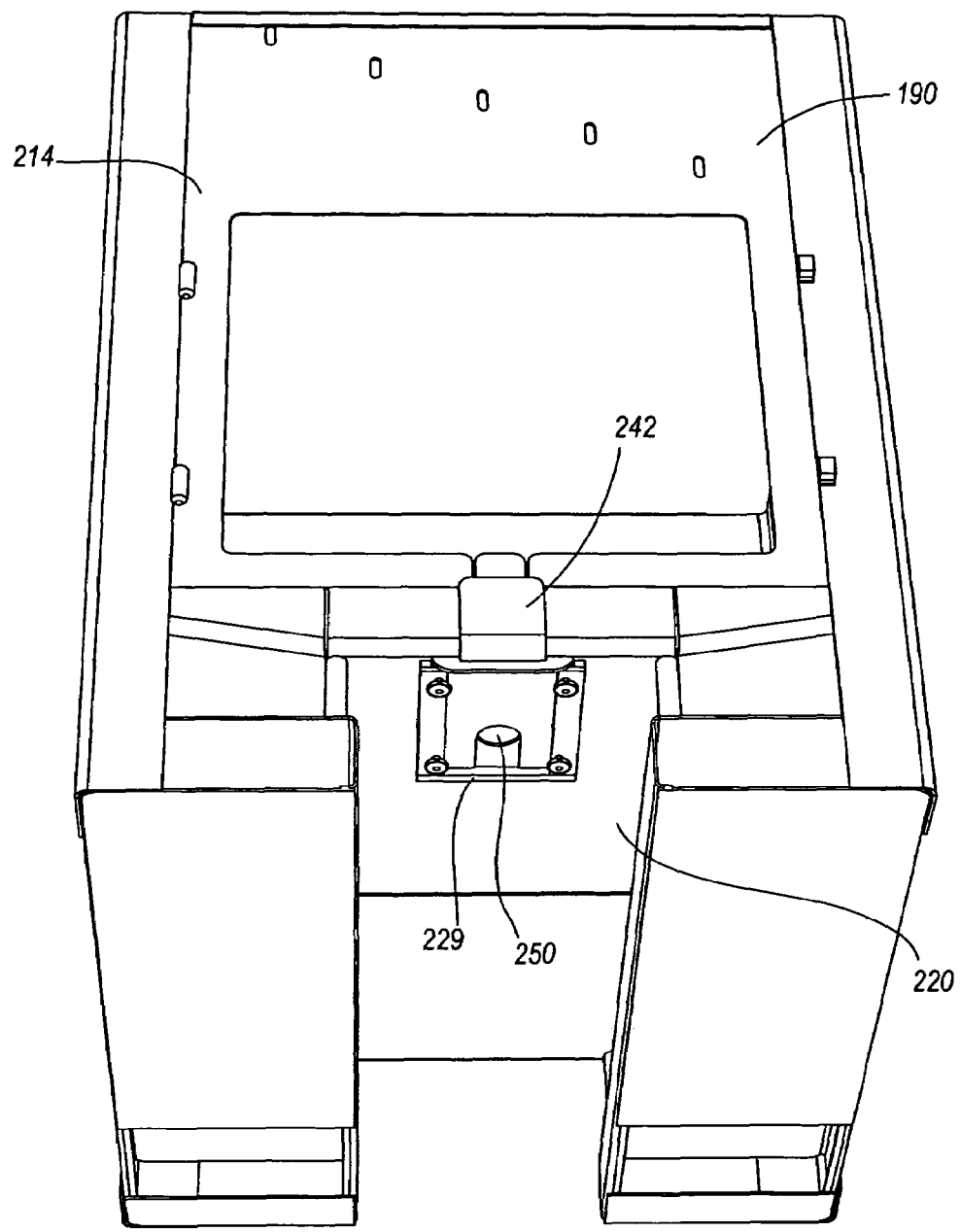
FIG. 16 is a bottom perspective view of the support bin shown in FIG. 11 with the door removed.

As depicted in FIG. 16, retention plate 242 is mounted to base floor 220 by sliding side edges 246 and 247 of base plate 252 (FIG. 15) into corresponding channels 238 of brackets 236A and B (FIG. 14). Using handle 248, retention plate 242 is advanced within channels 238 until retention plate 242 contacts stop plate 229. In this position, rounded notches 223 and 244 are aligned so as to form a circular portal 250 which extends through base floor 220. The remainder of slot 230 on floor 198 and front panel 190 is covered by retention plate 242. Overlay 420 is received within slot 230 so as to substantially fill in slot 230, thereby forming a smooth transition with the remainder of interior surface 204. It is noted that tongue 424 of retention plate 242 is disposed inside of door 216 when door 216 is closed. As a result, retention plate 242 is supported by door 216 when a load is applied against retention plate 242 from within support bin 184. Finally, retention plate 242 is secured in position by manually tightening fasteners 239 so that shafts 240 bear against retention plate 242.

It is appreciated that support bin 184 can have a variety of different configurations. For example, in contrast to having door 216 hingedly mounted, door 216 can be mounted on rails so as to selectively slide up or down. Furthermore, slot 230 can be designed to only extend through floor 198 and not pass through fixed panel 214. In yet other embodiments, base plate 252 of retention plate 242 can comprise two or more discrete plates having notches which combine to form two or more portals that receive corresponding ports on pooling bag 256. Examples of alternative embodiments for support bin 184 are disclosed in U.S. patent application Ser. No. 10/810,156, filed on Mar. 26, 2004 in the names of Gregory P. Elgan et al. and entitled Fluid Dispensing Bins and Related Methods which application is incorporated herein by specific reference.

During assembly, pooling bag assembly 186 is brought into filtration room 44 of second housing 12. Packing bags 194 and 196 (FIG. 10) are removed from around pooling bag assembly 186. Door 216 on support bin 184 is opened and pooling bag assembly 256 is passed though doorway 219 into chamber 206. Fill line assembly 356, still retained within bag 392, is slid within slot 230 so that fill line assembly 356 extends below floor 198 of support bin 184. In this position, outlet port 294 is positioned within notch 223 on floor 198. Retention plate 242 is then mounted on floor 198 as discussed above so that slot 230 is substantially closed by retention plate 242 except for portal 250 through which outlet port 294 of pooling bag 256 extends. Pooling bag 256 is thus supported on floor 198 and retention plate 242.

Fill lines 362A and B are now removed from bag 392 and extended through opening 63 in wall 62 (FIG. 3). Notches are formed on window 65 so that window 65 can be closed with the fill lines 362A and B passing through the notches. Window 65 need only loosely bound fill lines 362A and B in that the air flow is always from clean room 58 to filtration room 44. Each filling bell 382 is then positioned within laminar hood 62 located within clean room 58. In the embodiment depicted, fill line assembly 356 tees into the two separate fill lines 362A and B prior to passing through opening 63. In an alternative embodiment, transition tube 360 can be extended to pass through opening 63 prior to teeing into the two fill lines. Again, where only one fill line is desired, no tee is required.

Final filter 167 of pooling bag assembly 186 is lifted out of support bin 184 and mounted to filter rack 164. Final filter 167 is then fluid coupled with the preceding filter 166D. Finally, circulation line 310 of pooling bag assembly 186 is connected to pump 316 as discussed above. In alternative embodiments, it is appreciated that pooling bag assembly 186 need not be preassembled and sterilized. For example, the various lines and components can be assembled on site and the sterilized by steam, vapor, chemical, or local radiation.

During operation, the bottles of thawed unfiltered serum are manually opened and poured into compartment 134 of fill bag 88 through filter 156 (FIG. 5). Pump 178 draws the unfiltered serum out of fill bag 88 and passes it though the train of filters 166, through final filter 167, and into chamber 262 of pooling bag 256 (FIGS. 4 and 6). However, prior to passing the now filtered serum into pooling bag 256, the air within filters 166 is first removed. This is accomplished by initially clamping closed fluid line 298 which extends between final filter 167 and pooling bag 256. The bleed valve 173 for each filter 166 is opened and a flask positioned below each bleed valve 173. When the pump 178 is initially activated, the serum flowing into the filters pushes the air out through the bleed valves 173. The air does not pass between adjacent filters because filter membrane 174 does not allow air to pass therethrough. Once serum starts passing through a corresponding bleed valve 173, the bleed valve is closed. The serum collected in the flask below the bleed valve is then poured back into fill bag 88. When all of the air is removed from each of filters 166, fluid line 298 is opened. As such, the only air that passes into pooling bag 256 is the air within final filter 167 and fluid line 298. This air, however, was already sterilized with the sterilization of pooling bag assembly 186.

As the unfiltered serum is pumped out of fill bag 88, additional unfiltered serum is poured into fill bag 88. Because fill bag 88 does not function to pool the batch of unfiltered serum, fill bag 88 can be significantly smaller than pooling bag 256. In an alternative embodiment, however, fill bag 88 can also be sized to simultaneously hold and pool the entire batch of unfiltered serum. During filtering of the serum, hose clamps 373 on fill lines 362A and B are closed (FIG. 9). As a result, all of the serum passing through filters 166 and 167 is collected within pooling bag 256. Because pooling bag 256 is empty and collapsed at the time of placement, pooling bag 256 slowly inflates as the filtered serum passes therein.

The above filtration process is continued until all of the first batch of serum has passed through fill bag 88 and pump 178. Once pump 178 runs dry, the flow of fluid through filters 166 and 167 stops. However, depending on the size of filters 166 and 167, several liters of serum can be retained within filters 166 and 167. Part of the serum is held within capsule 168 of the filter on the inlet side of filter membrane 174 while the remainder of the serum has passed through membrane 174 and is thus held on the outlet side of membrane 174.

To recoup the serum remaining within filters 166 and 167, first end 162 of second fluid line 161 is disconnected from pump 178. Pressurized air is then delivered into second fluid line 161 through first end 162. The air forces the serum within second fluid line 161 and within capsule 168 on the inlet side of filter membrane 174 to pass through filter membrane 174 of first filter 166A. In so doing, a corresponding volume of serum is displaced downstream through filters 166 and 167 and dispensed into pooling bag 256. First filter 166A is then disconnected from second filter 166B. Any serum remaining within first filter 166A on the inlet side of filter membrane 174 is removed through drain valve 171 into a collection container. The serum within first filter 166A on the outlet side of filter member 174 is also dispensed into the collection container. This can be accomplished by inverting first filter 166A and pouring the serum out though outlet port 172. Alternatively, each filter 166 can be made with a drain port that is fluid coupled with the outlet side of filter membrane 174. The serum dispensed into the collection container is termed residual serum.

Once first filter 166A is disconnected from second filter 166B, pressurized air is applied to inlet port 170 of second filter 166B. Again, the air forces the serum on the inlet side of filter membrane 174 of second filter 166B to pass through the filter membrane 174, thereby displacing more filtered serum into pooling bag 256. Second filter 166B is then disconnected from third filter 166C. The residual serum within second filter 166B is then also drained into the collection container. The above process is then repeated for the remainder of filters 166. Finally, the pressured air is applied to final filter 167 so as to force the fluid through filter membrane 154 thereof. Final filter 167, however, is not disconnected from pooling bag 256 until all of the filtered serum is drained from pooling bag 256. Final filter 167 is then removed and any residual serum therein drained into the collection container. The residual serum for each different batch is collected and then subsequently filtered and pooled as a separate batch that is specially labeled.

As a result of the above processing, substantially all of the original 1,000 liters of the first batch of serum, after filtration, is simultaneously disposed within pooling bag 256. This isolated collection of the filtered serum produces a true pool of the filtered serum. Pump 316 is then activated so that the filtered serum within pooling bag 256 is continually mixed. As a result, the filtered serum becomes and remains homogeneous.

It is appreciated that in alternative embodiments two or more different types of liquids can be poured into fill bag 88 for a given batch. For example, two or more different types of serum, such as calf and fetal bovine serum, can be added into fill bag 88 for a single batch. In still other embodiments, one or more liquids and/or one or more dissolvable solids can be introduced into fill bag 88 for a given batch. Conventional mixing systems can be used to mix the contents within fill bag 88 to dissolve the solids. Here it is noted that because the batch is pooled within pooling bag 256, the different liquids and/or dissolvable solids can be added at any time or concentration within fill bag 88.

Figure 17:
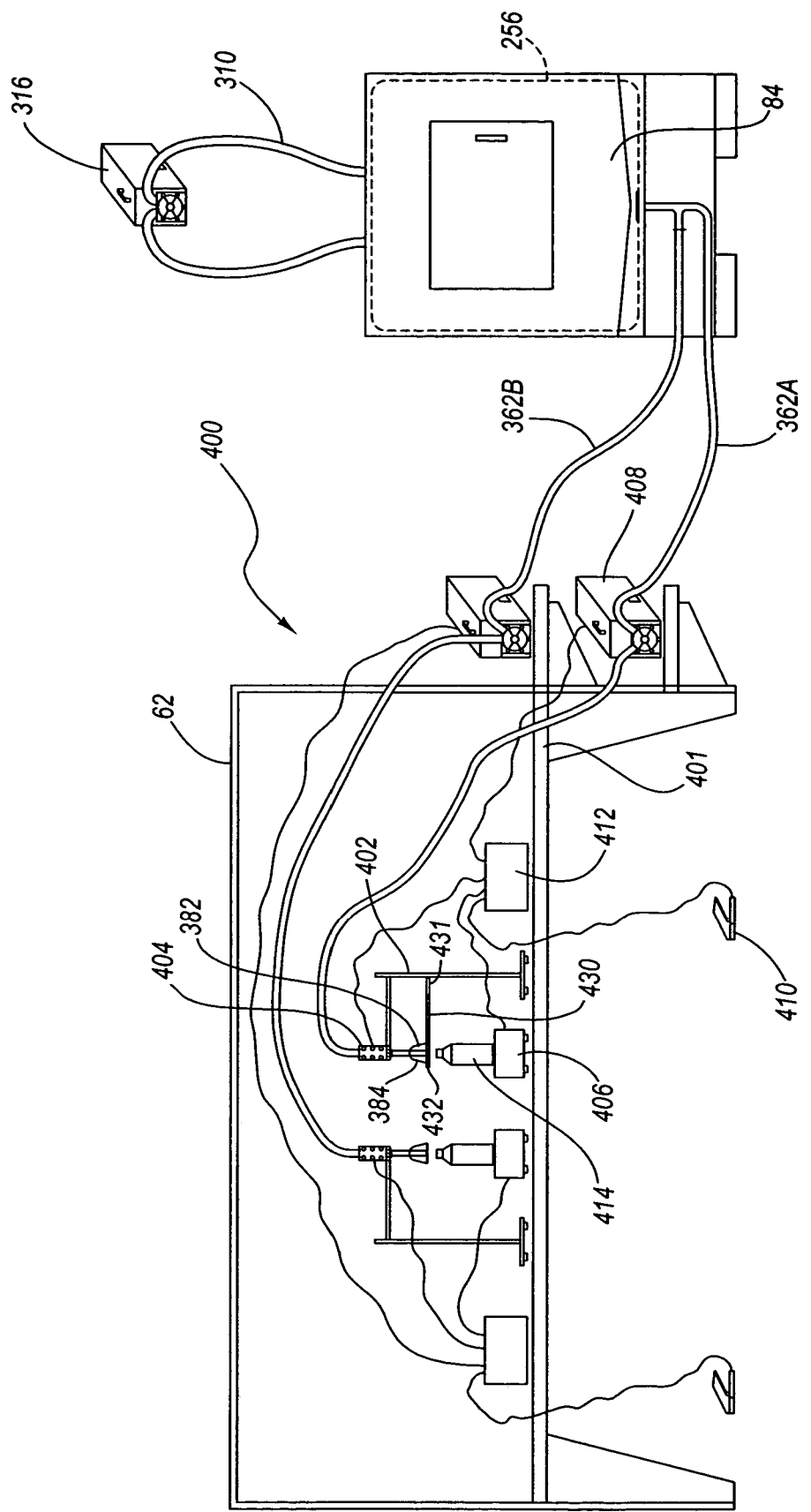
FIG. 17 is a front view of the pooling container assembly shown in FIG. 4 used in dispensing a liquid into bottles within the clean room of the second housing shown in FIG. 3.

Turning to FIG. 17, each fill line 362A and B operates with a separate dispensing system 400. As each dispensing system 400 is the same, dispensing system 400 will only be discussed with regard to fill line 362A. Specifically, laminar hood 62 includes a table top 401. A stand 402 is disposed within laminar hood 62 on table top 401. An electronic pinch valve 404 is mounted on stand 402. The end of fill line 362A is mounted on pinch valve 404 so that filling bell 382 suspends from stand 402.

Although not required, in one embodiment a retainer 430 has a first end 431 mounted on stand 402 and an opposing second end 432 secured to shroud 384 of filling bell 382. Second end 432 of retainer 430 can be selectively rotated so that filling bell 382 is tipped at a select angle and retained at that position. By tipping filling bell 382, the serum dispensed from filling bell 382, as discussed below in greater detail, can be directed to pass through the mouth of a bottle and then hit against the side interior surface of the bottle near the top of the bottle. The serum then flows down along the side interior surface of the bottle to the bottom of the bottle where the serum is collected. This processes minimizes foaming of the serum within the bottle. That is, if the serum is dispensed directly to the bottom of the bottle as opposed to the side interior surface thereof, the serum entering the serum collected at the bottom of the bottle can cause air to become entrained within the collected serum and thus cause foaming.

A scale 406 is positioned on table top 401 directly below filling bell 382. Fill line 362A is also coupled with a peristaltic pump 408 disposed within clean room 58. Hose clamps 373 are released on fill lines 362 such that operation of peristaltic pump 408 causes the filtered serum to be drawn out of pooling bag 256 and passed through fill lines 362. Finally, a foot pedal 410 is disposed below table top 401. Each of pinch valve 404, scale 406, peristaltic pump 408, and foot pedal 410 are in electrical communication with a central processing unit (CPU) 412.

During dispensing, an operator sits in front of table top 401 and places a presterilized bottle 414 on scale 406. The open mouth of bottle 414 is disposed below nozzle 386 and is covered by shroud 384. Shroud 384 prevents any unwanted material that might be floating within laminar hood 62 from falling into or being drawn into bottle 414 during filling. As discussed above, shroud 384 can be tipped. In one embodiment bottle 414 is comprised of PETE or PETG although other materials can also be used. Bottle 414 is typically sized to hold 125 ml, 500 ml or 1 liter. Other sizes can also be used. CPU 412 is inputted with the desired fill volume for bottle 414 and the known density of the serum. The operator steps on foot pedal 410 which in turn causes CPU 412 to instruct peristaltic pump 408 to rotate a set number of times so as to dispense a predetermined first volume of filtered serum into bottle 414. Once the first volume is dispensed, pinch valve 404 is then activated so as to pinch fill line 362A closed, thereby preventing any serum from leaking out of nozzle 386.

The first volume of filtered serum dispensed into first bottle 414 is slightly a more than the desired fill volume. Once the first volume is dispensed, scale 406 measures the weight of bottle 414 containing the first volume of filtered serum. Based on the weight of the first volume and the known density of the serum, CPU 412 is able to determine how many times peristaltic pump 408 should rotate so as to dispense the desired fill volume into the next bottle. The number of times peristaltic pump 408 rotates to dispense the desired fill volume varies slightly during the filling process due to the head pressure on the filtered serum within fill line 362A. That is, the head pressure within fill line 362A is highest when pooling bag 256 is filled with serum and decreases as the level of serum decreases within pooling bag 256. In turn, as the head pressure decreases, the number of turns needed to dispense the desired fill volume incrementally increases. It is noted that the diameter of fill line 362A is decreased, as discussed above, in that peristaltic pump 408 can more accurately measure and dispense fluids when it operates with smaller tubing.

Once first bottle 414 is filled and weighed, the operator removes first bottle 414 from scale 406 and screws a cap thereon. A second bottle 414 is then placed on scale 406. Again, based on the weight of the serum in first bottle 414, CPU 412 instructs peristaltic pump 408 to rotate a select number of times so as to fill second bottle 414 with the desired fill volume. Scale 406 then weighs the volume of serum within second bottle 414. In turn, this weight is used by CPU 412 to determine how many times peristaltic pump 408 need to rotate to dispense the desired fill volume into the next bottle. As such, the weight of the serum in a prior bottle 414 is used to adjust the rotation of peristaltic pump 408 so that the desired fill volume is dispensed into each bottle, within acceptable tolerances, as the head pressure within fill line 362 drops. The process is continually repeated to fill empty bottles until all of the serum is removed from pooling bag 256.

In one embodiment of the present invention, means are provided for dispensing a predetermined quantity of fluid through fill line 362. One example of such means includes the system as discussed above which includes the scale, CPU, and pump. It is appreciated, however, that a variety of other systems can also be used. For example, in one alternative the scale can be eliminated. Alternative types of pumps can then be used that can precisely measure the desired fill volume. In yet other embodiments, various sensors can be used to measure the actual head pressure. The CPU can thus use the known fluid pressure when activating the peristaltic pump. In still other embodiments, the dispensing can be based on weight. That is, the CPU can instruct the pump to stop when the scale measures a predefined weight. Other techniques known in the art can also be used.

When desired, CPU 412 can be programmed to fill bottles 414 of a variety of different sizes for a given batch of pooled filtered fluid. By way of example and not by limitation, for a given batch of one thousand liters, the fluid can be dispensed into five hundred 1 liter bottles, five hundred 500 ml bottles and two thousand 125 ml bottles. The 125 ml bottles can then be used for quality control, retention, and quality assurance purposes.

Returning to FIG. 3, to advance filled bottle 414 the operator within clean room 58 opens first door 72 of pass-through portal 70 and places bottle 414 within pass-through portal 70. First door 72 is then closed. An operator within packing room 64 then opens second door 74 and removes filled bottle 414 from pass-through portal 70. Second door 74 is then closed. As previously discussed, clean room 58 is placed under a positive air pressure relative to packing room 64 so that air always flows from clean room 58, through pass-through portal 70, to packing room 64, thereby preventing contamination from entering clean room 58 through pass-through portal 70. Within packing room 58, the operator uses a screw device to torque down the cap on bottle 414. The operator then heat shrinks a seal around the cap and places a label on bottle 414.

Once sealed, bottle 414 is placed on a transportable cart 416 within packing room 64. When cart 416 is filled with bottles of filtered serum, cart 416 is transported to freezer room 28 of first housing 10 through an outer door 426 and an inner door 428 (FIG. 2). Again, outer door 426 provides protection for inner door 428 during transport and can be eliminated. It is desirable to quickly freeze the filtered serum so as to prevent separation or settling of the filtered serum within bottles 414. As such, it is desirable to freeze the filtered serum within a 12 hour period. To accomplish this, freezer room 28 is held at a temperature of −20° C. Other temperatures and freezing periods can also be used. Once frozen, bottles 414 are removed to a separate long term storage facility for subsequent sale.

In one embodiment, particularly where there is a significant delay being filtering the first batch and a second batch, once all of the first batch of serum is bottled, used pooling bag assembly 186, filters 166, fill bag 88 and fluid lines 160 and 161 are removed and replaced with a new bag assembly 186, filters 166, fill bag 88 and fluid lines 160 and 161. The only structure that is reused and needs to be cleaned because it directly contacts the serum is diaphragm pump 178.

In alternative embodiments, where a second batch of serum has been thawed so as to be processed directly after the first batch, it is envisioned that each of used pooling bag assembly 186, filters 166, fill bag 88 and fluid lines 160 and 161 could be reused. Alternatively, select components such as pooling bag assembly 186 and/or filters 166 could be replaced between different batches.

In the illustrated embodiment where the liquid being filtered is fetal bovine serum, it is generally not necessary to take samples for in-process testing or quality control or for retention and quality assurance at any point upstream of the dispensing system 400. In other embodiments, however, especially when more than a single liquid is introduced into fill bag 88, a port for withdrawing such samples can be provided either upstream of filters 166,167, such as on fluid line 160 or 161, or downstream of that filters 166,167, such as on fluid line 298. The port allows samples to be taken and tested.

In some applications, operation of the pump 178, and/or other fluid flows, can be stopped or reduced to a subnormal rate until the test results have been completed and, if appropriate, additional materials added to fill bag 88 to bring the tested parameter into a desired range or value. In some instances, fill bag 88 holds at any one time no more than a fraction (e.g., one third or one quarter) of the fluid for an entire batch. Each sub-batch of unfiltered fluid within bag 88 is tested before being pumped by pump 178 through the filtration system. Pump 316 is operated to create and maintain homogeneity within pooling bag 256 as soon as the first batch of filtered fluid has reached an appropriate partially-full level within pooling bag 256.

The depicted embodiment is primarily directed towards a system that minimizes cleaning between processing of different batches. In alternative embodiments, however, it is appreciated that some or all of the disposable components can be replaced with corresponding reusable components that require cleaning between uses. For example, pooling bag 256 and/or fill bag 88 can be replaced with stainless steel containers. Likewise, the various fluid lines can be replaced with fixed stainless steel lines while the disposable cartridges for filters 166 can be replaced with reusable stainless steel housing.

Furthermore, in the depicted embodiment, because pooling bag assembly 186 is presterilized, no in situ sterilization of components and/or connections is required. In alternative embodiments, however, it is appreciated that the various components of pooling bag assembly 186 can be assembly within filter room 44 and then sterilized by conventional process such as steam, vapor, chemical, or local radiation.

It is also appreciated that in alternative embodiments filtration facility 8 need not include both of housings 10 and 12 or can include duplicates of housing 10 and 12. For example, some storage facilities may include a fixed thaw room and quick freezer room. In these embodiments, filtration facility 8 may only comprise second housing 12 because all of the required elements for filtering and pooling the fluid to achieve and maintain homogeneity are contained within second housing 12. As such, only second housing 12 needs to be transported to the storage facility to filter the serum or other fluids. In yet other embodiments where a storage facility has a large supply of serum or other fluids that must be filtered quickly, duplicates of housing 10 and/or 12 can be transported to the storage facility to expedite filtering. It is also appreciated that each of housing 10 and 12 can have a variety of different designs. For example, each of housing 10 and 12 can comprise a plurality of small housings that are designed to function as separate units or can be selectively coupled together during use. For example, each separate room or combination of rooms could be formed from a separate housing.

Furthermore, when the mobile filtration facility of the present invention is used to filter and pool other fluids such as human blood serum or plasma or fractions, appropriate temperature controls can be built into second housing 12. As such, there would be no need for the thawing or refreezing steps associated with first housing 10. Thus, for example, staging room 40 in second housing 12 can receive individual bags of human blood serum which had previously been collected for transfusion purposes and stored cold, but were beyond their expiration dates for use in transfusion purposes. The blood could still be pooled, adjusted with various components and used as clinical chemistry control materials or various other in vitro diagnostics or research purposes.

Once all of the serum has been processed at the storage facility, filtration facility 8 can be transported to a next storage facility for processing the serum thereat. In this regard, filtration facility 8 can be transported to a variety of different locations within a given country and/or to a variety of different countries around the world. Filtration facility 8 thus provides a quick, efficient and economical way of filtering serum or other fluids at locations around the world while eliminating the need to build, operate, and maintain a fixed filtration facility. Because the serum or other fluids can be maintained at or proximate to the location where the fluid was initially harvested or produced, use of the inventive filtration facility 8 eliminates the need to obtain import licenses and provides greater ease in documenting origin and history of filtered serum or other fluid.

In still other embodiments, it is envisioned that filtration facility 8 can be shipped to a designated location and permanently maintained thereat. For example, this can be done at a remote location or in third world countries where it may be difficult to build a clean room. It is also appreciated that the above disclosure of the present invention comprises a number of discrete inventions that can be used independently or in combination with other systems. For example, filtration system 50 or the discrete components thereof are not limited to being used in a mobile filtration facility but can also be used in a conventional fixed facility having a clean room and/or filtration system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for filtering a liquid derived from mammalian blood, the method comprising:

transporting a mobile filtration facility to a first storage facility housing a liquid derived from mammalian blood, the mobile filtration facility comprising a mobile first housing bounding at least a substantially sterile clean room and a filtration area separated from the clean room;

delivering a first batch of the liquid into a disposable fill bag located within the filtration area of the first housing;

processing the liquid located within the fill bag through at least one filter and into a disposable pooling bag so as to obtain a true pool of the first batch of the liquid within the pooling bag; and dispensing the filtered liquid located within the pooling bag into a plurality of packaging containers located within the clean room.

2. A method as recited in claim 1, wherein the first batch of unfiltered liquid is initially frozen, the method comprising thawing the first batch of the liquid prior to delivering the first batch of the liquid into the disposable fill bag.

3. A method as recited in claim 2, further comprising thawing the entire first batch of the liquid within a thaw room of the mobile filtration facility.

4. A method as recited in claim 3, wherein the mobile filtration facility comprises a mobile second housing bounding the thaw room.

5. A method as recited in claim 1, wherein the act of delivering the first batch of the liquid comprises pouring the first batch of the liquid through a screen and into the fill bag.

6. A method as recited in claim 1, further comprising continuously mixing the filtered liquid within the pooling bag while the filtered liquid is being dispensed into the packaging containers.

7. A method as recited in claim 1, wherein the liquid derived from mammalian blood comprises serum, plasma, or fractions thereof.

8. A method as recited in claim 1, wherein the act of processing the liquid comprises pumping the liquid through at least one prefilter having a filter membrane with a porosity in a range from about 0.2 μm to about 10 μm and through at least one final filter having a filter membrane with a porosity of about 0.1 μm, the at least one prefilter being fluid coupled in series with the at least one final filter.

9. A method as recited in claim 1, wherein the act of dispensing the filtered liquid comprises:

dispensing a first volume of the filtered liquid into a first packaging container;

weighing the packaging container containing the first volume; and dispensing a second volume of the filtered liquid into a second packaging container, the second volume being based on the weight of the packaging container containing the first volume.

10. A method as recited in claim 1, wherein the first housing bounds a packaging room that is separated from the clean room by a partition wall, a double door pass-through conduit is formed on the partition wall, the method further comprising transferring the packaging containers containing the liquid from the clean room to the packaging room through the pass-through conduit.

11. A method as recited in claim 1, wherein the mobile filtration facility comprises a mobile second housing bounding a freezer room, the packaging containers containing the filtered liquid being frozen within the freezer room of the mobile second housing.

12. A method as recited in claim 1, further comprising:

replacing the fill bag, at least one filter, and pooling bag with a new fill bag, at least one filter, and pooling bag, respectively; and delivering a second batch of the liquid into the new fill bag.

13. A method as recited in claim 1, further comprising:

transporting the mobile filtration facility to a second storage facility housing liquid derived from mammalian blood; and using the mobile filtration facility to filter the liquid of the second storage facility.

14. A method as recited in claim 1, wherein the second storage facility is in a separate country from the first storage facility.

* * * * *

UNITED STATES PATENT AND TRADEMARK OFFICE
CERTIFICATE OF CORRECTION

PATENT NO. : 7,326,355 B2  
APPLICATION NO. : 10/929275  
DATED : February 5, 2008  
INVENTOR(S) : Graetz et al.

Page 1 of 1

It is certified that error appears in the above-identified patent and that said Letters Patent is hereby corrected as shown below:

Column 12
Line 41, change "fluid.  lines" to --fluid lines--

Column 16
Line 44, change "194 and 196" to --394 and 396--

Signed and Sealed this

Second Day of September, 2008

JON W. DUDAS  
*Director of the United States Patent and Trademark Office*